(12) United States Patent
Gallop et al.

(10) Patent No.: US 6,368,874 B1
(45) Date of Patent: Apr. 9, 2002

(54) METHODS FOR HARD-TAGGING AN ENCODED SYNTHETIC LIBRARY

(75) Inventors: Mark A. Gallop, Los Altos; Eric Gordon, Palo Alto; Zhi-Jie Ni, Sunnyvale; Derek MacLean, Los Altos; Christopher Holmes, Sunnyvale; William Fitch, Palo Alto; Nikhil Shah, Fremont, all of CA (US)

(73) Assignee: Affymax, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/442,427

(22) Filed: Nov. 17, 1999

Related U.S. Application Data

(63) Continuation of application No. 09/103,968, filed on Jun. 24, 1998, now abandoned, which is a continuation of application No. 08/577,203, filed on Dec. 22, 1995, now Pat. No. 5,846,839.

(51) Int. Cl.$^7$ ............................................. G01N 33/543
(52) U.S. Cl. ..................... 436/518; 436/501; 436/528; 436/85; 435/7.1; 435/DIG. 1; 435/DIG. 2; 435/DIG. 14; 435/DIG. 15; 435/DIG. 16; 435/DIG. 17; 435/DIG. 18; 435/DIG. 21; 435/DIG. 49; 536/23.1
(58) Field of Search ................................ 436/518, 501, 436/528, 85; 435/7.1, DIG. 1, DIG. 2, DIG. 14, DIG. 15, DIG. 16, DIG. 17, DIG. 18, DIG. 21, DIG. 49; 536/23.1

(56) References Cited

U.S. PATENT DOCUMENTS 5,846,839 A * 12/1998 Gallop et al. ................ 436/518

FOREIGN PATENT DOCUMENTS

| WO | WO 93/06121 | 4/1993 | ............ C07H/21/00 |
|---|---|---|---|
| WO | WO 94/08051 | 4/1994 | ............ C12Q/1/68 |
| WO | WO 95/35278 | 12/1995 | .......... C07D/207/12 |
| WO | WO 96/00148 | 1/1996 | .............. B32B/9/04 |
| WO | WO 96/00391 | 1/1996 | ............ G01N/33/53 |

OTHER PUBLICATIONS

Brenner et al. (1992), "Encoded combinatorial chemistry," Proc. Natl. Acad. Sci. 89:5381–5383.

Farina et al. (1993), "Palladium–catalyzed coupling of aryl-stannanes with organic sulfonates: A comprehensive study," J. Org. Chem. 58:5434–5444.

Furka et al. (1991), "General method for rapid synthesis of multicomponent peptide mixtures," Int. J. Peptide Protein Res. 37:487–493.

Gallop et al. (1994), "Applications of combinatorial technologies to drug discovery. 1.Background and peptide combinatorial libraries," J. Med. Chem. 37:1233–1251.

Gordon et al. (1994), "Applications of combinatorial technologies to drug discovery. 2. Combinatorial organic synthesis, library screening strategies, and future directions," J. Med. Chem. 37:1385–1401.

Kerr et al. (1993), "Encoded combinatorial peptide libraries containing non–natural amino acids," J. Am. Chem. Soc. 115:2529–2531.

Lebl et al. (1995), "One–bead–one–structure combinatorial libraries," Biopolymers (Peptide Science) 37:177–198.

Martin et al. (1982), "Fused silica capillary gas chromatography/negative chemical ionization mass spectrometry for determination of catecholamines and their 0–methylated metabolites," Anal. Chem. 54:1806–1811.

Needels et al. (1993), "Generation and screening of an oligonucleotide–encoded synthetic peptide library," Proc. Natl. Acad. Sci. USA 90__10700–10704.

Nikolaiev et al. (1993), "Peptide–encoding for structure determination of nonsequence–able polymers within libraries synthesized and tested on solid–phase supports," Peptide Research 6:161–170.

Ohlmeyer et al. (1993), "Complex synthetic chemical libraries indexed with molecular tags," Proc. Natl. Acad. Sci. USA 90:10922–10926.

Safar et al. (1995), "Amino–acid like subunits based on iminodiacetic acid and their application in linear and DKP libraries," Proc. Eur. Pept. Symp., $23^{rd}$, 471–472.

* cited by examiner

*Primary Examiner*—Padmashri Ponnaluri
(74) *Attorney, Agent, or Firm*—Townsend and Townsend and Crew LLP

(57) ABSTRACT

Disclosed are chemical encryption methods for determining the structure of compounds formed in situ on solid supports by the use of specific amines tags which, after compound synthesis, can be deencrypted to provide the structure of the compound found on the support.

19 Claims, 11 Drawing Sheets

Coding Scheme for Pyrrolidine Library

| Amino Acids | Gly | Ala | Phe | Leu |
|---|---|---|---|---|
| Ethylbutyl |  | O | O |  |
| Dibutyl | O |  | O |  |
| Dipentyl | O | O |  | O |

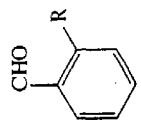

| Aldehydes (R) | H | OMe | Me | OTBDMS |
|---|---|---|---|---|
| Methylhexyl | O | O | O |  |
| Methylheptyl | O | O | O |  |
| Methyldodecyl |  |  |  | O |

| Olefins | MA | MMA | TBA | MVK | AN |
|---|---|---|---|---|---|
| Dihexyl | O | O | O |  |  |
| Dioctyl |  | O |  | O | O |
| Bis(2-ethyl)hexyl |  |  | O |  | O |

MA=methyl acrylate; MMA=methyl methacrylate; TBA=*tert*-butyl acrylate; MVK=methyl vinyl ketone; AN=acrylonitrile

Fig. 11

METHODS FOR HARD-TAGGING AN ENCODED SYNTHETIC LIBRARY

CROSS-REFERENCE

This application is a continuation of U.S. application Ser. No. 09/103,968 filed Jun. 24, 1998 (now abandoned), which is a continuation of U.S. application Ser. No. 08/577,203 filed Dec. 22, 1995 (now U.S. Pat. No. 5,846,839).

BACKGROUND OF THE INVENTION

Field of the Invention

This invention relates to the chemical encryption of the structure of compounds formed in situ on solid supports by the use of specific amine tags which, after compound synthesis, can be deencrypted to provide the structure of the compound found on the support.

The solid supports of this invention find particular utility in preparing encoded synthetic libraries of compounds on the support for facilitating screening of these compounds for biological activity.

REFERENCES

The following publications and patent applications are cited in this application as superscript numbers:

1 M. A. Gallop, R. W. Barrett, W. J. Dower, S. P. A. Fodor and E. M. Gordon, *J. Med. Chem.*, 37:1233 (1994)
2 E. M. Gordon, R. W. Barrett, W. J. Dower, S. P. A. Fodor and M. A. Gallop, *J. Med. Chem.*, 37:1385 (1994)
3 A. Furka, F. Sebestyen, M. Asgedom and G. Dibo, *Int. J. Peptide Protein Res.*, 37:487 (1991)
4 W. J. Dower, R. W. Barrett and M. A. Gallop, International Patent Application Publication No. WO 93/06121 (1993)
5 S. Brenner and R. A. Lerner, *Proc. Natl. Acad. Sci., USA*, 89:5181 (1992)
6 J. M. Kerr, S. C. Banville and R. N. Zuckermann, *J. Am. Chem. Soc.*, 115:2529 (1993).
7 V. Nikolaiev, A. Stierandova, V. Krchnak, B. Seligmann, K. S. Lam, S. E. Salmon and M. Lebl, *Pept. Res.*, 6:161 (1993)
8 M. C. Needels, D. G. Jones, E. M. Tate, G. L. Heinkel, L. M. Kochersperger, W. J. Dower, R. W. Barrett and M. A. Gallop, *Proc. Natl. Acad. Sci., USA*, 90: 10700 (1993)
9 M. H. J. Ohlmeyer, R. N. Swanson, L. W. Dillard, J. C. Reader, G. Asouline, R. Kobayashi, M. Wigler and W. C. Still, *Proc. Natl. Acad. Sci. USA*, 90:10922 (1993)
10 C. P. Holmes, International Patent Application Serial No. PCT/US95/07988 for "Methods for the Solid Phase Synthesis of Thiazolidinones, Metathiazanones, and Derivatives Thereof", filed Jun. 23, 1995
11 Lebl, et al., *Peptide Science*, February 1995
12 Campbell, et al., International Patent Application Serial No. PCT/US95/07964, for "Methods for the Synthesis of Diketopiperazines", filed Jun. 23, 1995
13 Gallop, et al., International Patent Application Serial No. PCT/US95/07878, for "Methods for Synthesizing Diverse Collections of Pyrrolidine Compounds", filed Jun. 22, 1995
14 Gallop, et al., U.S. patent application Ser. No. 08/264,136 for: "Methods for Synthesizing Diverse Collections of β-Lactam Compounds", filed Nov. 21, 1995
15 Farina, et al., *J. Med. Chem.*, 3:877 (1991)
16 Stills, et al., International Patent Application Serial No. PCT/US93/09345 for "Complex Combinatorial Chemical Libraries Encoded with Tags", filed Oct. 1, 1993

All of the above publications and patent applications are herein incorporated by reference in their entirety to the same extent as if each individual publication, patent or patent application was specifically and individually indicated to be incorporated by reference in its entirety.

STATE OF THE ART

Synthetic chemical libraries produced by combinatorial synthesis have rapidly become important tools for pharmaceutical lead discovery and compound optimization.[1,2] Typically, combinatorial synthesis is conducted via a multi-step synthesis to provide a library of target compounds. Each step in this synthesis involves a chemical modification of the then existing molecule formed from the previous step wherein one can vary the choice of reagents and/or reaction conditions to provide for a variety of different target compounds. For example, such steps could include the use of different building blocks to form different compounds, the use of different inorganic or organic reagents which alter where the building blocks are added or the stereochemistry of the addition, etc.

Many of the combinatorial approaches devised to prepare such libraries rely on solid-phase synthetic techniques and exploit the efficient "split/pool" method to assemble all possible combinations of a set of chemical building blocks.[3] The "split/pool" method employs a pool of solid supports which contains or can be derivatized to contain reactive moieties for forming the molecules of interest tethered to the solid support. This pool is initially split and each split pool is then subjected to a first reaction which reaction results in different modifications to each of the pools. After reaction, the pools of solid supports are combined and the pooled supports are then again split. Each split pool is subjected to a second reaction which is different for each of the pools. The process is continued until a library of target compounds are formed on the solid supports.

The reactions employed at each stage of this synthesis can include the addition of different building blocks to the solid support, the use of different reagents and/or reaction conditions to differentially alter the existing chemical entity on the solid support, etc. Also combinations of different building blocks with different reagents and/or reaction conditions can also be employed.

The "split/pool" protocol is particularly well-suited to the generation of large libraries, and the synthetic target compounds may be screened for interaction with macromolecular receptors either in binding assays where the compounds remain tethered to their synthetic supports, or in soluble assays after cleavage of the compounds from the resin. Elucidation of the chemical structure of biologically active library members has represented a major challenge because the quantity of material available for chemical analysis from a complex library is frequently minuscule.

A general solution to this structure elucidation problem has been proposed that exploits a set of surrogate analytes, or identifier tags, which can be detected with either greater ease and/or sensitivity than the chemical entities which they represent.[4] Through their concurrent appendage to the synthesis supports, these tags provide an unambiguous record of chemical reaction history and/or chronology of monomer (building block). additions to each support in the library. This method, which has become known as encoded combinatorial synthesis[5], has broad scope and utility, and conceptually may be applied to the construction of any collection of compounds that can be produced through a multi-step scheme of synthesis on solid supports.

Two conceptually different approaches to encoding a combinatorial synthesis have been described. In the first mode, the sequence of monomer addition steps is recorded by the parallel and alternating assembly of a polymeric molecule that is itself amenable to chemical sequence analysis. Here the structure of any combinatorial product is reflected by the sequence of a single cognate identifier tag on the solid support. Both peptides[6,7] and oligonucleotides[8] have been sucessfuly used in this manner to encode the synthesis of polyamide combinatorial libraries, the tags being analyzed by, for example, Edman or dideoxy Sanger sequencing respectively.

In the second encoding method, a set of readily identifiable unique markers employed for each reaction step is attached to the solid support to identify which reaction was visited in which step of the target compound synthesis on that particular support.[4,9] The set of identifiable markers is employed in binary code format with each set identifying a different monomer and/or reaction conditions. For example, each marker can be represented in binary code format by either a "0" for its absence or a "1" for its presence. Accordingly, if 3 different identifiable markers are employed in a first set, this set contains 7 unique binary code combinations (the binary code represented by 000 is not used). Specifically, the binary codes for these combinations employing markers A, B and C would read as follows:

| SUBCOMBINATIONS FOR MARKERS A, B AND C | BINARY CODE FOR THIS SUBCOMBINATION |
| --- | --- |
| A | 001 |
| B | 010 |
| C | 100 |
| A, B | 011 |
| A, C | 101 |
| B, C | 110 |
| A, B, C | 111 |

In this example, the use of 7 different building blocks for a given step in the "split/pool" synthesis could be encoded by the above set of 3 markers using the 7 different combination of these markers. Each different combination of markers provides a "tag" for a particular building block used in the synthesis.

As is apparent, increasing the number of markers from 3 to 10 in the set would increase the number of unique binary combinations for that set to over 1000. The large number of combinations is necessary since an n-step synthesis using m building blocks at each step requires that total of m×n monomer-specific steps be separately identified.

Removal of all markers from the solid support and identification of their presence or absence identifies the particular tag defined by that marker combination and, accordingly, the relevant information concerning the monomer addition. In this embodiment, the compounds employed as identifiable markers in the encryption set must be distinguishable from each other in order to be capable of accurate deencryption and the compounds employed in a first set must be different from the compounds employed in a second set in order to maintain strict correlation between the encryption/deencryption information.

Central to this approach is the understanding that the binary code provides for a significantly larger pool of possible tag combinations than a monomeric code. For example, if the synthetic scheme encodes for three different reaction steps, the use of 30 unique compounds in three sets of 10 identifiable markers each would encode for at least $1000^3$ or $10^9$ possible combinations. In this regard, Still, et al.[9] have described how a series of 18 chromatographically resolvable different halocarbon derivatives can be appended to a synthesis resin in a binary coding strategy, and subsequently liberated for analysis by electron capture gas chromatography to code for a library of 117,649 peptides.

Essential requirements with any scheme of encoded combinatorial synthesis on solid supports is that the chemistries employed in compound synthesis and tag addition steps be mutually compatible, that the tags remain on the support during each step of the synthesis, and that the tag uniquely identify a particular reaction step. An ideal tagging medium would, therefore, be one which reacts robustly with functional groups found on or attached to the resin so as to be incorporated thereon in high yield, which tagging reactions are completely chemically inert to the reaction intermediates and products employed in compound synthesis and, which tags are amenable to rapid and straightforward analysis at trace levels.

In this regard, considerable success has been achieved in using oligonucleotides as an enzymatically amplifiable coding moiety, and it has been demonstrated that the DNA tagging strategy is sufficiently versatile and robust to permit the automated synthesis of encoded libraries of glycopeptides, polycarbamates and thiazolidinones[10], in addition to polyamides. Nevertheless, since oligonucleotides do possess sites of chemical lability and the chemistry for oligonucleotide synthesis is not always compatible with compound synthesis especially of small molecules[1], there is a continuing need in the art to develop encoding strategies complementary to the synthesis of small organic molecule libraries.

SUMMARY OF THE INVENTION

This invention is directed to chemical entities useful as tags on solid supports to encode a target compound synthesized on the support. These tags are reactive with functional groups on or attached to the support and provide for an unambiguous record of the reaction history including the chronology of monomer (building block) additions during target compound synthesis on the support. Moreover, the tags are inert to the organic synthesis scheme employed to prepare the target compound on the support surface and can be deencrypted at an appropriate point in time in order to determine the structure of the target compound formed on the support.

More specifically, this invention is directed to the use of chemical tags and solids supports containing these tags covalently attached thereto. These tags are an amine or mixture of amine tags selected from a plurality of amines of formula Ia:

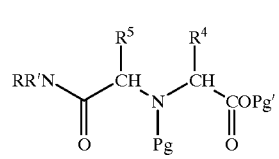

wherein R and R' are independently hydrocarbyl groups of from 1 to 30 carbon atoms which define a unique amine tag used to identify a reaction conducted in target compound synthesis and/or the point in time where said reaction was conducted; $R^4$ and $R^5$ are either hydrogen or are joined to form a piperidine ring; Pg is selected from hydrogen, an amine tag of formula Ia above bound to the amino nitrogen through the carbonyl functionality of formula Ia and a compatible protecting group provided that the compatible protecting group is orthogonal to any and all protecting groups employed in target compound synthesis, and Pg' is selected from —OH, an amine tag of formula Ia above bound to an amino nitrogen through the carbonyl functionality of formula Ia and —OPg" where Pg" is a compatible protecting group which is orthogonal to any and all protecting groups employed in target compound synthesis.

The amine compounds of formula Ia above are covalently attached to the solid support either directly or through a suitable linker arm through either the amine or carboxyl functionality.

In view of the above, in one of its composition aspects, this invention is directed to a solid support comprising multiple copies of a single target compound covalently attached thereto wherein the target compound is prepared in situ on the support by sequentially conducting at least two reactions wherein each of the reactions employed to prepare said target compound and/or the step in the chemical synthesis where said reaction is conducted is encoded by a tag covalently coupled to the support, immediately before or after each reaction, wherein said tag is an amine or mixture of amines selected from a plurality of amines of formula I

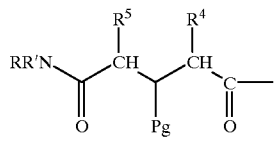

wherein R and R' are independently hydrocarbyl groups of from 1 to 30 carbon atoms which define a unique amine tag used to identify a reaction conducted in target compound synthesis and/or the point in time where said reaction was conducted; $R^4$ and $R^5$ are either hydrogen or are joined to form a piperidine ring; and Pg is selected from hydrogen, an amine tag of formula I above bound to the amino nitrogen through the carbonyl functionality of formula I and a compatible protecting group provided that the compatible protecting group is orthogonal to any and all protecting groups employed in compound synthesis, provided that each tag combination used to encode a first reaction and/or the point in time where said reaction is conducted is different from and distinguishable over all other tag combinations used to encode the remaining reactions and/or points in time where said reactions are conducted so as provide a binary or higher coding system wherein the code uniquely identifies the compound resulting from the reactions.

The amine compounds set forth above define a pool of compounds useful for forming sets of tags each set of which can encrypt for each variant employed in a single reaction involved in the synthesis of target compounds and/or the point in time where said reaction is conducted. In order to unequivocally resolve each encrypted tag, the compounds employed in each tag set must be different from and distinguishable over the compounds employed in the other sets.

In one embodiment, the tag is different than the other tags based on chemical identity. In this embodiment, the tag for a first reaction is selected to provide a unique combination from a plurality of individual amines compounds included within the selected set of these compounds. For example, if the first reaction merely employs different building blocks, a set of three compounds (markers) A, B and C provides for 7 unique tag combinations in binary code format (other than 000) for identifying the 7 different building blocks employed in this first reaction. Each unique tag combination unequivocally encrypts for each building block.

Chemically different tags include those having different chemical structures including both positional and stereochemical isomers as well as those having the same structure but which have, for example, radioisotopes at different locations in the molecular structure. The different radioisotopes can be distinguished from each other based on, for example, proton or $^{13}C$ nuclear magnetic resonance.

Ternary codes can be based on, for example, chemical identity and the presence of a compound at two different concentrations. In this case, the three states defining the ternary code would be the presence of the compound at two different and distinguishable concentrations or its absence. The advantage of higher order codes over a binary code is that fewer compounds are required to encode the same quantity of information about the synthesis or, using the same number of compounds, more information can be encoded.

Each amine compound is distinguishable over the remaining amine compounds based on some physical or chemical property. The distinguishing feature can be found in the compound itself or a derivative thereof and includes, by way of example, retention times on HPLC, nuclear magnetic spectrum profiles (either $^1H$ or $^{13}C$), mass spectroscopy, etc.

Preferably, when amines of formula I form the tag, the tags are constructed to form a polymeric amide on the solid support which polymeric amide has the formula

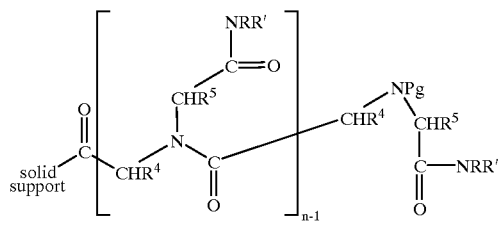

wherein the polymeric amide is covalently attached to the solid support either directly or through a linker arm and further wherein each R and R' define a unique amine tag used to identify a reaction conducted in target compound synthesis and/or the point in time where said reaction was conducted, $R^4$ and $R^5$ are either hydrogen or are joined to form a piperidine ring, Pg is a compatible protecting group, and n represents the number of reactions encoding for the target compound synthesis provided that each amine tag combination employed to encode a single reaction is different from and distinguishable over all other amine tag combinations used to encode other variations used in that reaction and still further provided that the amines used to encode a first reaction are different from the amines used to encode the other encrypted reactions so as provide a binary or higher coding system wherein the code uniquely identifies the target compound resulting from monomer coupling.

These polymeric amides are formed from the monomeric amines of formula I merely by converting the Pg group to hydrogen and then reacting the resulting amine (—NH) with the carboxyl group (or activated carboxyl group) of a second monomeric amine compound of the formula RR'NC(O)CH$_2$NPgCH$_2$COOH wherein R, R' and Pg are as defined above. For n encryptions, this process is repeated n times. At this point, the terminal amine of the polymeric amide contains a —NPg group which can be readily deblocked to provide the —NH group.

The use of such polymeric amides permits chemical deencryption simply by breaking the amide bonds to form a plurality of n sets of different amines which are then analyzed to determine the presence or absence of specific amines.

In view of the above, in another of its composition aspects, this invention is directed to a solid support comprising multiple copies of a single target compound covalently attached thereto wherein the target compound is prepared in situ on the support by sequentially conducting at least two reactions wherein each of the reactions employed to prepare said target compound and/or the step in the chemical synthesis where said reaction is conducted is encoded by a monomeric unit of a polymeric amide of the formula

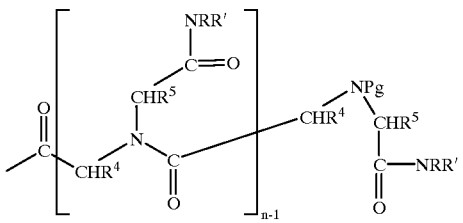

wherein the polymeric amide is covalently attached to the solid support and further wherein R and R' of each monomeric unit define a unique amine tag used to identify a reaction conducted and/or the point in time when said reaction was conducted in the target compound synthesis, Pg is a compatible protecting group, $R^4$ and $R^5$ are either hydrogen or are joined to form a piperidine ring, and n represents the number of reactions encoding for the target compound synthesis provided that each amine compound employed in tags to encode a single reaction and/or point in time when said reaction is conducted is different from and distinguishable over all other amine compounds employed in tags used with the other encryptions so as provide a binary or higher coding system wherein the code uniquely identifies the target compound resulting from the reactions conducted on the solid support.

In one of its method aspects, this invention is directed to a method for tagging a solid support having multiple copies of a single target compound covalently attached thereto in order to determine the structure of the target compound attached to the support wherein the compound is prepared in situ on the support by sequentially conducting n reactions on said support wherein n is an integer greater than 1 which method comprises:

a) conducting a first reaction on the solid support wherein the first reaction and/or the step in the chemical synthesis where said reaction is conducted is encoded by a tag coupled to the support, immediately before or after coupling of each monomer, wherein said tag is an amine or mixture of amines selected from a plurality of amines of formula I

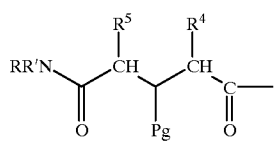

I wherein R and R' are independently hydrocarbyl groups of from 1 to 30 carbon atoms which define a unique amine tag used to identify the reaction 4F conducted in target compound synthesis and/or the point in time where said reaction is conducted; $R^4$ and $R^5$ are either hydrogen or are joined to form a piperidine ring; and Pg is selected from hydrogen, an amine tag of formula I above bound to the amino nitrogen through the carbonyl functionality of formula I, a compatible protecting group provided that the compatible protecting group is orthogonal to any and all protecting groups employed in compound synthesis, and hydrogen provided that one of the Pg groups is hydrogen provided that each tag combination employed to encode a single reaction is different from and distinguishable over all other tag combinations used to encode other variations used in that reaction and still further provided that the amine compounds used to encode a first reaction are different from the amine compounds used to encode the other encrypted reactions so as provide a binary or higher coding system; and b) repeating procedure a) above until all n steps for target compound synthesis on the support are completed.

The tags described above are particularly useful for encoding target compounds prepared in libraries via combinatorial chemistry wherein each support contains multiple copies of a single target compound. Accordingly, in this embodiment, this invention is directed to a library of target compounds bound to a solid support wherein each support comprises multiple copies of a single target compound covalently attached thereto wherein each target compound in the library is prepared in situ on the support by sequentially conducting at least two reactions wherein at least one of the reactions conducted to prepare a first target compound is different from the reactions conducted to prepare the remaining target compounds and further wherein each of the reactions conducted to prepare each target compound and/or the step in the chemical synthesis where said reaction is conducted is encoded by a tag coupled to the support having said compound bound thereto, immediately before or after coupling of each monomer, wherein said tag is an amine or mixture of amines selected from a plurality of amines of formula I

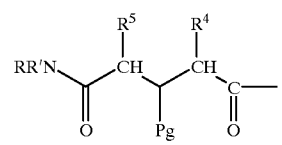

I wherein R and R' are independently hydrocarbyl groups of from 1 to 30 carbon atoms which define a unique amine tag used to identify the reaction conducted in target compound synthesis and/or the point in time where said reaction is conducted; $R^4$ and $R^5$ are either hydrogen or are joined to form a piperidine ring; and Pg is selected from hydrogen, an amine tag of formula I above bound to the amino nitrogen through the carbonyl functionality of formula I and a compatible protecting group provided that the compatible protecting group is orthogonal to any and all protecting groups employed in compound synthesis provided further that each tag combination employed to encode a single reaction is different from and distinguishable over all other tag combinations used to encode other variations used in that reaction and still further provided that the amine compounds used to encode a first reaction are different from the amine compounds used to encode the other encrypted reactions so as provide a binary or higher coding system.

BRIEF DESCRIPTION OF THE DRAWINGS

FIGS. 9–11 illustrate the formation of encoded pyrrolidine libraries.

DETAILED DESCRIPTION OF THE INVENTION

Figure 1:
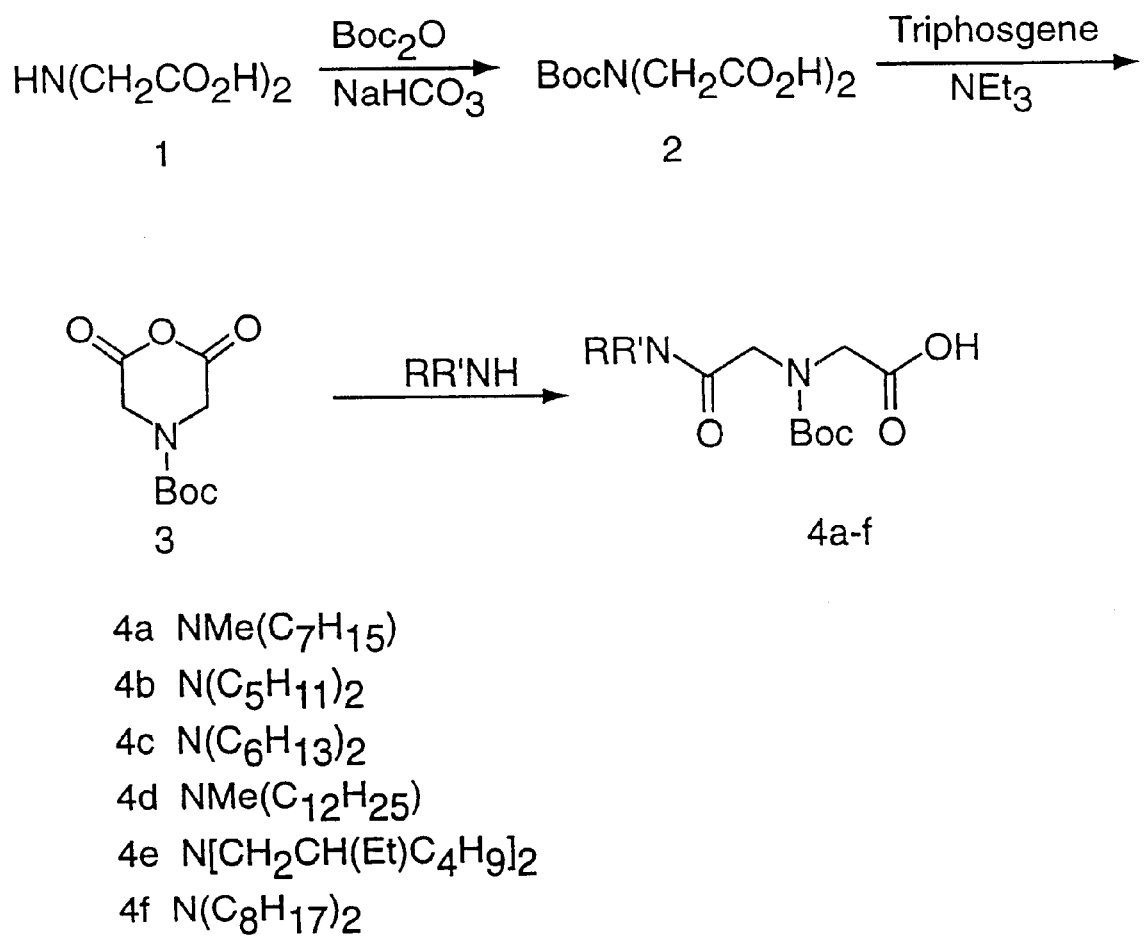
FIG. 1 illustrates the synthesis of amine compounds of formula I.

This invention is directed to chemical entities useful as tags on solid supports to encode a target compound synthesized on the support. At the appropriate time, the tags are deencrypted to provide for structure of the target compound on the surface of the solid support.

Prior to discussing this invention in further detail, the following terms will first be defined:

The term "substrate" or "solid support" refers to a material having a rigid or semi-rigid surface which contain or can be derivatized to contain reactive functionality which covalently links a compound to the surface thereof. Such materials are well known in the art and include, by way of example, silicon dioxide supports containing reactive Si—OH groups, polyacrylamide supports, polystyrene supports, polyethyleneglycol supports, and the like. Such supports will preferably take the form of small beads, pellets, disks, or other conventional forms, although other forms may be used. In some embodiments, at least one surface of the substrate will be substantially flat.

The term "reactions" refers to any reaction which adds a monomer to the solid support, which modifies the chemical entity formed after monomer addition to the solid support and/or which removes a group from the solid support. The reactions can employ monomers (building blocks) which becomes incorporated onto the solid support or can merely employ a reagent such as heat, base, acid, an oxidizing agent or a reducing agent which does not become incorporated into the structures found on the support. Modifications of the chemical entity formed after monomer addition to the solid support includes, for example, cyclization, isomerization, etc. Removal of a group from the solid support includes hydrolysis to remove an ester, removal of protecting groups, etc.

The term "target compound" refers to the compound or a group of compounds to be synthesized on the solid support and subsequently screened for biological activity or other properties.

The term "monomers" as used relative to compound synthesis refers to discreet building blocks employed to prepare the target compound. Thus, in the case of thiazolidone compound synthesis on a solid support by reaction of an amine, an aldehyde and a thioacetic acid compound as reported by Holmes[10], each of the amine, aldehyde and thioacetic acid is a monomer in the synthesis of the thiazolidone. In the case of peptide synthesis, the monomer is typically an amino acid but can comprise a di- or higher amino acid fragment of the target peptide which is incorporated as a single entity.

One of the monomers employed in the synthesis is or becomes covalently attached to the solid support such that the target compound resulting from the synthetic scheme employed is covalently attached to the support. Preferably, such covalent attachment is through linking arms. Suitable linking arms are well known in the art and include, by way of example only, conventional linking arms such as those comprising ester, amide, carbamate, ether, thio ether, urea, amine groups and the like.

The linking arm can be cleavable or non-cleavable. "Cleavable linking arms" refer to linking arms wherein at least one of the covalent bonds of the linking arm which attaches the target compound to the solid support can be readily broken by specific chemical reactions thereby providing for target compounds free of the solid support ("soluble compounds"). The chemical reactions employed to break the covalent bond of the linking arm are selected so as to be specific for bond breakage thereby preventing unintended reactions occurring elsewhere on the target compound or the tag. The cleavable linking arm is selected relative to the synthesis of the compounds to be formed on the solid support (i.e., target compounds or tags) so as to prevent premature cleavage from the solid support as well as not to interfere with any of the procedures employed during compound synthesis on the support.

Suitable cleavable linking arms are well known in the art and FIGS. 9A–9D illustrates several embodiments of such linking arms. Specifically, FIG. 9A illustrates a cleavable Sasrin resin comprising polystyrene beads and a cleavable linking arm as depicted therein which linking arm is cleaved by strong acidic conditions such as trifluoroacetic acid. Cleavage results in breakage at the vertical line interposed between the oxygen and carbonyl moieties of the ester so as to provide for a compound terminating in a carboxylic acid.

FIGS. 9B and 9C illustrate cleavable TentaGel TENTAGEL AC and TENTAGEL, PHB, each of which is a polystyrene-polyethyleneglycol graft copolymer, with a benzylic hydroxyl synthesis handle resins respectively, each comprising a polystyrene bead and the cleavable linking arm depicted therein both of which are cleaved by strong acidic conditions such as trifluoroacetic acid. Cleavage results in breakage at the vertical line interposed between the oxygen and carbonyl moieties of the ester so as to provide for a compound terminating in a carboxylic acid.

FIG. 9D illustrates a cleavable TENTAGEL RAM, a polystyrene-polyethyleneglycol graft copolymer with a NH-FMOC synthesis handle. resin comprising a polystyrene bead and a cleavable linking arm depicted therein which is cleaved by strong acidic conditions such as trifluoroacetic acid. Cleavage results in breakage at the wavy line interposed between the nitrogen and the benzhydryl carbon of the linking arm so as to provide for a compound terminating in an amide group. In this case, this linking arm facilitates formation of the amide bond by stabilizing the intermediate carbonium ion on the carbon atom between the two aromatic groups. Such stabilization permits selective bond cleavage as compared to bond cleavage for other amide groups, if any, of the compound.

Reversible covalent cleavable linkages can be used to attach the molecules to the support. Examples of suitable reversible chemical linkages include (1) a sulfoester linkage provided by, e.g., a thiolated tagged-molecule and a N-hydroxy-succinimidyl support, which linkage can be controlled by adjustment of the ammonium hydroxide concentration; (2) a benzylhydryl or benzylamide linkage provided by, e.g., a Knorr linker, which linkage can be controlled by adjustment of acid concentration; (3) a disulfide linkage provided by, e.g., a thiolated tagged-molecule and a 2-pyridyl disulfide support (e.g., thiolsepharose from Sigma), which linkage can be controlled by adjustment of the DTT (dithiothreitol) concentration; and (4) linkers which can be cleaved with a transition metal (e.g. HYCRAM).

The linker may be attached between the tag and/or the molecule and the support via a non-reversible covalent cleavable linkage. For example, linkers which can be cleaved photolytically can be used. Preferred photocleavable linkers of the invention include those recited in U.S. patent application Ser. No. 08/374,492, filed, Jan. 17, 1995, 6-nitro-veratry-oxycarbonyl (NVOC) and other NVOC related linker compounds (see PCT patent publication Nos. WO 90/15070 and WO 92/10092; see also U.S. patent application Ser. No. 07/971,181, filed Nov. 2, 1992, incorporated herein by reference); the ortho-nitrobenzyl-based linker described by Rich (see Rich and Gurwara (1975) *J. Am. Chem. Soc.* 97:1575–1579; and Barany and Albericio (1985) *J. Am. Chem. Soc.* 107: 4936–4942) and the phenacyl based linker discussed by Wang. (see Wang (1976) *J. Org. Chem.*, 41:3258; and Bell of and Mutter (1985) *Chimia* 39:10).

"Non-cleavable linking arms" refer to linking arms wherein the covalent bonds linking the target compound to the solid support can only be cleaved under conditions which chemically alters unintended parts of the structure of the target compound or tag attached thereto.

The term "hydrocarbyl" refers to an organic radical composed of carbon and hydrogen which may be aliphatic, alicyclic, aromatic or combinations thereof (e.g., arylalkyl). Preferably, the hydrocarbyl group is saturated, i.e., contains no ethylene and acetylenic unsaturation, particularly acetylenic unsaturation.

The term "stereoisomer" refers to a chemical compound having the same molecular weight, chemical composition, and constitution as another, but with the atoms grouped differently. That is, certain identical chemical moieties are at different orientations in space and, therefrom, when pure, have the ability to rotate the plane of polarized light. However, some pure stereoisomers may have an optical rotation that is so slight that it is undetectable with present instrumentation. The compounds described herein may have one or more asymmetrical carbon atoms and therefore include various stereoisomers. All stereoisomers are included within the scope of the invention.

The term "compatible protecting group" or "protecting group" refers to a chemical group that exhibits the following characteristics: 1) reacts selectively with the desired functionality in good yield to give a derivative that is stable to the projected reactions for which protection is desired; 2) can be selectively removed chemically and/or enzymatically from the derivatized solid support to yield the desired functionality; and 3) is removable in good yield by reagents compatible with the other functional group(s) generated in such projected reactions. Examples of protecting groups can be found in Greene et al. (1991) *Protective Groups in Organic Synthesis*, 2nd Ed. (John Wiley & Sons, Inc., New York). Preferred protecting groups include photolabile protecting groups (such as methylnitropiperonyloxycarbonyl (Menpoc), methylnitropiperonyl (Menp), nitroveratryl (Nv), nitroveratryloxycarbonyl (Nvoc), or nitroveratryloxymethyl ether (Nvom)); acid-labile protecting group (such as Boc or DMT); base-labile protecting groups (such as Fmoc, Fm, phosphonioethoxycarbonyl (Peoc, see Kunz (1976) *Chem. Ber.* 109:2670); groups which may be removed under neutral conditions (e.g., metal ion-assisted hydrolysis ), such as DBMB (see Chattopadhyaya et al. (1979) *J.C.S. Chem. Comm.* 987–990), allyl or alloc (see,.e.g., Greene and Wuts, "Protective Groups in Organic Synthesis", 2nd Ed., John Wiley & Sons, Inc., New York, N.Y. (1991), 2-haloethyl (see Kunz and Buchholz (1981) *Angew. Chem. Int. Ed. Enal.* 20:894), and groups which may be removed using fluoride ion, such as 2-(trimethylsilyl)ethoxymethyl (SEM), 2-(trimethylsilyl)ethyloxycarbonyl (Teoc) or 2-(trimethylsilyl)ethyl (Te) S (see, e.g., Lipshutz et al. (1980) *Tetrahedron Lett.* 21:3343–3346)); and groups which may be removed under mild reducing conditions (e.g., with sodium borohydride or hydrazine), such as Lev. Id. at 30–31, 97, and 112. Particularly preferred protecting groups include Fmoc, Fm, Menpoc, Nvoc, Nv, Boc, CBZ, allyl, alloc (allyloxycarbonyl), Npeoc (4-nitrophenethyloxycarbonyl), Npeom (4-nitrophenethyloxymethyloxy), α,α-dimethyl-3, 5-dimethoxybenzyloxycarbonyl (ddz) and trityl groups. The particular removable protecting group employed is not critical.

The term "orthogonal protecting groups" refer to two compatible protecting groups which, in the presence of each other, can be differentially removed or, if not differentially, removed, can be differentially reprotected. In one embodiment, it may be desirable to remove all of the protecting groups in one step such as at completion of the synthesis.

The term "distinguishable over" as it relates to each compound employed with the tags means that each compound provides a unique detectable property distinguishing it from other compounds. Such unique detectable properties can include, by way of example, a different elution time in HPLC, GC, etc. for a specific eluant; a unique molecular weight or degradation pattern detectable by mass spectroscopy; a unique nuclear magnetic resonance peak; a unique fluorescence; etc. For example, a unique nuclear magnetic resonance (NMR) peak can be achieved by selectively labeling a single carbon atom in an amine compound with $^{13}C$ with other amine compounds having the same hydrocarbyl groups but having different carbon atoms so labeled. The high population of $^{13}C$ coupled with its downfield shift in $^{13}C$-nmr would identify of the specific compound employed.

The term "chemical library" or "array" refers to an intentionally created collection of differing target compounds or molecules which can be prepared either synthetically or biosynthetically and screened for biological activity in a variety of different formats (e.g., libraries of soluble compounds; and libraries of compounds tethered to solid supports). The term is also intended to refer to an intentionally created collection of stereoisomers. The library comprises at least 2 members, preferably at least 10 members, more preferably at least $10^2$ members and still more preferably at least $10^3$ members. Particularly preferred libraries comprise at least 104 members and more preferably at least 106 members.

The term "combinatorial synthesis strategy" or "combinatorial chemistry" refers to an ordered strategy for the parallel synthesis of diverse compounds by sequential addition of reagents (monomers) which leads to the generation of large chemical libraries. Thus, combinatorial chemistry refers to the systematic and repetitive, covalent connection of a set of different "monomers" of varying structures to each other to yield large arrays of diverse compounds or molecular entities.

The term "exogenous base" refers to non-nucleophilic bases such as alkali metal acetates, alkali metal carbonates, alkaline metal carbonates, alkali metal bicarbonates, tri (lower alkyl) amines, and the like, for example, sodium acetate, potassium bicarbonate, calcium carbonate, diisopropylethylamine, triethylamine, and the like.

I. METHODS FOR ENCRYPTING SOLID SUPPORTS

The binary coding schemes described herein employ compounds defined by the amines of formula I above. Sets comprising unique members (compounds) are then assembled into binary mixture to code for each of the reactions to be encrypted in the reaction scheme for target compound synthesis. Each set of compounds defines a group of amines wherein each member of the group is unique to that set.

The power of the binary coding method is that a great many target compounds can be unambiguously represented as binary combinations of just a few marker compounds. For example, if 21 different secondary amines define the amine compounds to be used for tagging and the synthetic scheme for compound synthesis employs 3 different reactions which are to be encrypted, then three sets of the amine compounds each having 7 unique members can be created. Further to this example, the 7 members of the each set define $2^7-1$ or 127 combinations in binary code with the absence of all members being excluded. That is to say that each set would be able to provide 127 different combinations of amines for each monomer thereby encoding for 127 different variations in each reaction. Since there are three reactions, the total number of encrypted variations possible and hence the total number of encrypted target compounds which can be encoded by this method is $127^3$ or over 2 million members.

The tags coupled to each solid support are unique to the reactions visited on the support (including the monomer employed and/or the point in the synthetic scheme where this monomer was employed). The ability to encrypt the structure of the compound on the solid support finds particular utility in combinatorial chemistry where there is generated a library of solid supports, each having multiple copies of a single compound on the surface thereof. Biological or pharmaceutical testing of this library typically reveals activity for only a small percentage of compounds in the library. The ability to deencrypt the solid supports on which the active compounds were synthesized greatly facilitates drug discovery because there is simply no need to evaluate inactive compounds.

Deencryption of these tags is simply made by, for example, detecting the tags coupled to the solid support. Again, for example, if amines A–U are used to encrypt the target compounds synthesized in a three step process, a first set of amines A–G could encode for 127 different variations in this first reaction, a second set of amines H–N could encode for 127 different variations in the second reaction, and a third step of amines O–U could encode for 127 variations in the third reaction. When the amines coupled to the solid support are identified, the particular combination of amines A–G detected from the support defines the specific first reaction conducted on that support; the particular combination of amines H–N detected from the support defines the specific second reaction conducted on the support, and the particular combination of amines O–U detected from the support defines the specific third reaction conducted on the support. This is all the information needed to determine the unique reaction history visited on that support.

Detection of the amine compounds from a particular support can be achieved by identifying that unique detectable property of each compound. Such properties include, by way of example, a different elution time in HPLC, GC, etc. for a specific eluant; a unique molecular weight or degradation pattern detectable by mass spectroscopy; a unique nuclear magnetic resonance peak; a unique fluorescence; etc.

II. ENCRYPTION METHODS USING AMINE TAGS

The binary code scheme of this invention includes specific amine compounds which react robustly to form chemically stable bonds having protecting groups orthogonal to those employed in target compound synthesis on the solid support. The robust reaction of these amines coupled with the chemically stable bonds formed therefrom provide for "hard tagging" of the solid supports which infers that these amine compounds are not labile during synthesis of the target compound to the solid supports. Accordingly, these amines are compatible with the synthetic schemes employed in conventional organic synthesis of a multiplicity of target compounds including, by way of example, with solid phase synthesis of libraries of diketopiperazines[12], thiazolidinones[10], metathiazanones[10], pyrrolidines[13], β-lactams[14], etc., as well as with peptide and DNA synthesis on solid supports. The particular target compound employed in the solid phase synthesis on the solid support is not critical provided that the tagging chemistry is compatible or made to be compatible therewith.

The amine compounds of formula I are readily prepared from iminodiacetic acid when $R^4$ and $R^5$ are hydrogen. Specifically, iminodiacetic is conventionally protected with a removable protecting group followed by anhydride formation via contact with, for example, thiophosgene and an exogenous base. Opening of the anhydride by reaction with an approximate stoichiometric amount or slight excess of a secondary amine compound yields compounds of formula I. In this regard, the removable blocking group employed on the amine should be compatible with this reaction. For example, an Fmoc protecting group on the amine of the anhydride will rapidly deprotect in the presence of the secondary amine. Accordingly, a compatible removable blocking group such as Boc is employed at this step.

FIG. 1 illustrates a specific embodiment of synthesizing the amine compounds prior to coupling to the solid support. Specifically, in this method, iminodiacetic acid 1 is contacted with di-tert-butyl dicarbonate and an exogenous base (sodium carbonate) in a suitable inert diluent to provide for Boc protected derivative, compound 2. Compound 2 is then contacted with triphosgene and exogenous base (triethylamine) to form the cyclic anhydride 3 which is ring opened by reaction with a secondary amine compound to form the particular N-protected amines 4a–f of formula I. The different amines employed to create compounds 4a–f define the pool of tag compounds which pool can readily be enlarged simply by increasing the number of amines employed.

Figure 8:
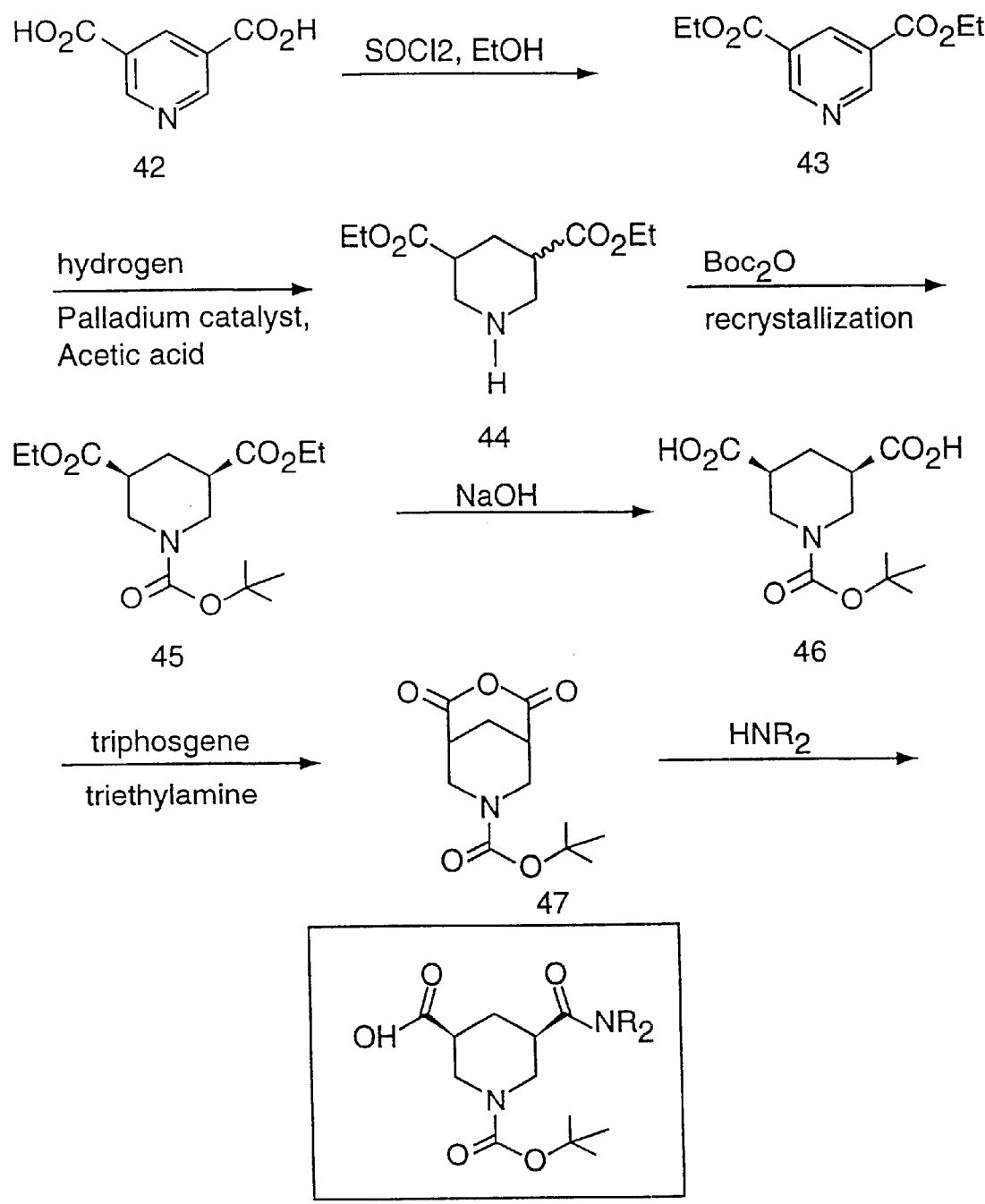
FIG. 8 illustrates the formation of amine tags of formula I wherein $R^4$ and $R^5$ are joined to form a piperidine ring.

The amine tags of formula I wherein $R^4$ and $R^5$ are joined to form a piperidine ring are readily prepared from pyridine-3,5-dicarboxylic acid by a several step process as illustrated in FIG. 8. Specifically, commercially available pyridine-3,5-dicarboxylic acid 42 is first esterified via thionyl chloride (SOCl2) in ethanol (EtOH) to provide for the 3,5-diethyl ester. Hydrogenation of this diester over palladium in acetic acid with 50 psi $H_2$ yields the diethyl ester of piperidine-3, 5-dicarboxyl acid as a cis/trans mixture which upon contact with di-tert-butyl dicarbonate in a suitable inert diluent provides for Boc protected derivative, compound 45 wherein the cis-isomer crystallizes from the mixture upon standing at room temperature or in a refrigerator. Removal of some impurities before the Boc protection is essential for the purification of the cis-isomer. Direct protection of the amine at the hydrogenation stage in dioxane by adding $Boc_2O$ into hydrogenation vessel saved one step, but the purification afterward was cumbersome. Saponification of the diester with potassium hydroxide in ethanol gave cis-diacid in 98% yield. Treatment of the cis-diacid with triphosgene in the presence of triethylamine gave the symmetric anhydride 47 in 91% yield. Anhydride 47 is now available for ring opening via a secondary amine in the manner described above to provide for compounds of formula I wherein $R^4$ and $R^5$ are joined to form a piperidine ring which are purified by washing with 0.1 N hydrochloric acid.

Figure 2:
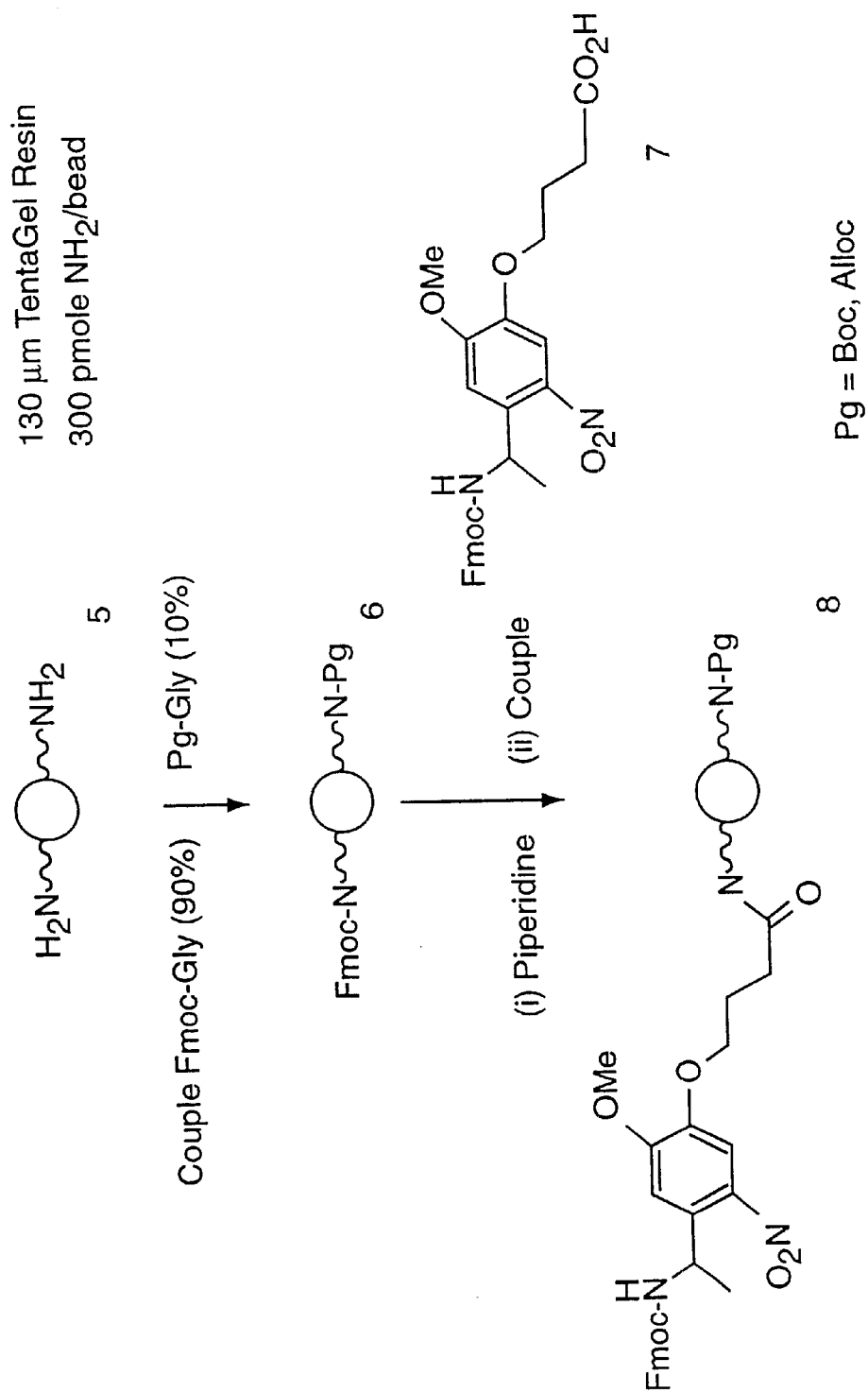
FIGS. 2–4 illustrate an example of tag incorporation onto a solid support and subsequent release of the tags from the solid support.

The chemistry for coupling these amine tags (whether $R^4$ and $R^5$ are hydrogen or joined to form a piperidine ring) to the solid support during compound synthesis starts with differentially functionalized sites for target compound synthesis and tag addition. These sites are defined by orthogonal protecting groups that permit the chemistry to be addressed unambiguously at either the target compound or tagging sites. FIG. 2 illustrates an example of orthogonal protection for target compound and amine tagging synthesis.

Specifically, in FIG. 2, solid support 5 having amino groups bound to the surface thereof is reacted with a molar equivalent (based on the amino groups on the resin surface) of a mixed coupling reagent. The mixed coupling reagent comprises a majority (e.g., greater than 50 molar % to about 98 molar %) of a compound coupling reagent providing the sites for target compound synthesis on the support and a minority (e.g., from about 2 molar % to less than 50 molar %) of a tag coupling reagent providing the sites for tag synthesis on the support. In this case, the coupling agent comprises 90 molar percent of Fmoc-Gly as the target compound coupling reagent and 10 molar percent of Pg-Gly as the tag coupling reagent where Pg is an amino protecting group orthogonal to Fmoc. The reaction is conventional and results in solid support 6 having about 90% of its surface amino groups coupled to Fmoc-Gly and about 10% of its surface amino groups having Pg-Gly coupled thereto assuming that Fmoc-Gly and Pg-Gly have similar chemical coupling rates. Conventional orthogonal deprotection of the Fmoc groups on solid support 6 using piperidine followed by coupling of Fmoc protected photolabile linker 7 yields solid support 5 which is now ready for target compound synthesis as well as tag coupling at chemically distinguishable sites.

Figure 3:
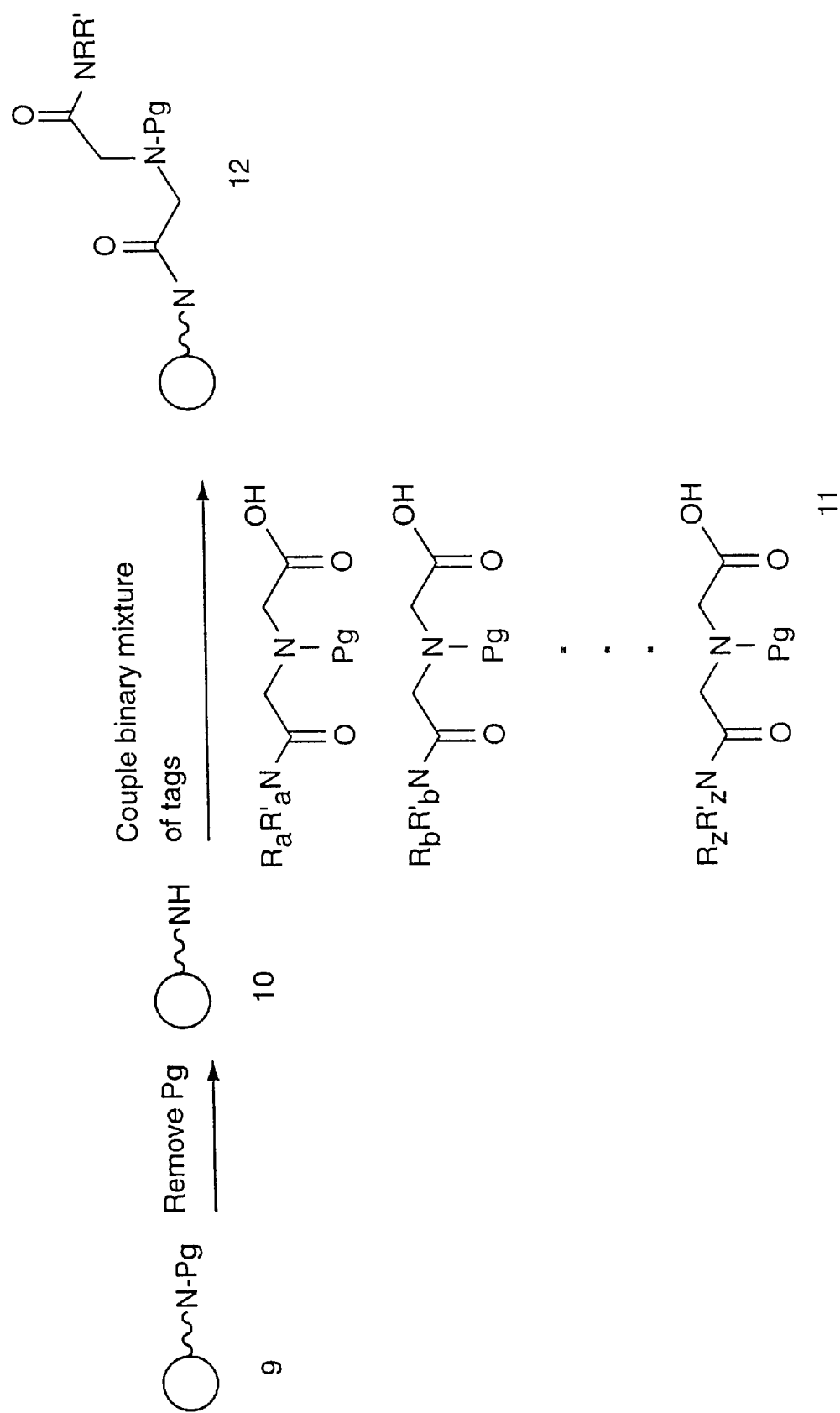

FIG. 3 illustrates one manner of tag coupling to the solid support. Because the protecting groups employed on the compound synthesis sites and the tag coupling sites of solid support 8 (FIG. 2) are orthogonal, tag coupling is conducted either immediately before or immediately after each reaction encrypted for target compound synthesis. This is particularly important in combinatorial chemical synthesis where, at each step of a "split/pool" combinatorial synthesis, the reaction conducted at this step is recorded by the appropriate tag comprising a binary mixture of amines. As illustrated in FIG. 3, tag coupling is initiated by first identifying the particular combination of amine compounds which encrypt for the particular reactions to be encrypted. Next the orthogonal protecting group Pg is differentially removed from solid support 9 to expose the amino functionalities on the support 10. An activated ester of the particular combination of amines 11 defining the tag are then combined with support 10 under conditions sufficient to form amide 12. The combination of amines 11 employed as the tag provides for a combination of amides 12 on the solid support having the same components as the amines. It is understood, however, that the amine tag combination may include from a single amine to n amines where n is the number of amines employed in the set of amine compounds.

The activated esters of amine 11 can be either preformed prior to addition to solid support 10 or, depending upon compatibility of the Pg group, can be formed in situ from the amide/acid. In this regard, Alloc and Boc protecting groups are compatible with this alternative approach but Fmoc groups are not. This alternative method is attractive in that it avoids the need to pre-synthesize many tag monomers.

According to some embodiments, amides 12 are prepared through the coupling of an activated carboxyl group on amines 11. For example, the carboxyl group of amines 11 can be activated by conversion to an activated ester, such as the corresponding —ODhbt, —OSu or —OPfp. ester. Often these activated carboxyl groups are formed in situ. Techniques for producing these activated esters are well known in the art. Other embodiments will utilize a suitable coupling catalyst, such as DCC, DIC, HOBT, HATU, HBTU, BOP and PyBOP, to effect formation of amide 12.

Typically an excess of coupling reagent is used, with quantities ranging from 2 equivalents to 10 equivalents or more. Preferably 3 to 8 equivalents are employed. Often the degree of excess is determined with respect to the reactivity of the chemical species being coupled. Polar, aprotic solvents such as DMF, NMP, DMSO and methylene chloride are preferred. Reaction times may vary from 0.5 to 3 hours to overnight, and temperatures may vary from room temperature to reflux. In a preferred embodiment, the coupling is effected through the use of BOP and HATU, and optionally an exogenous base, such as DIEA.

Figure 4:
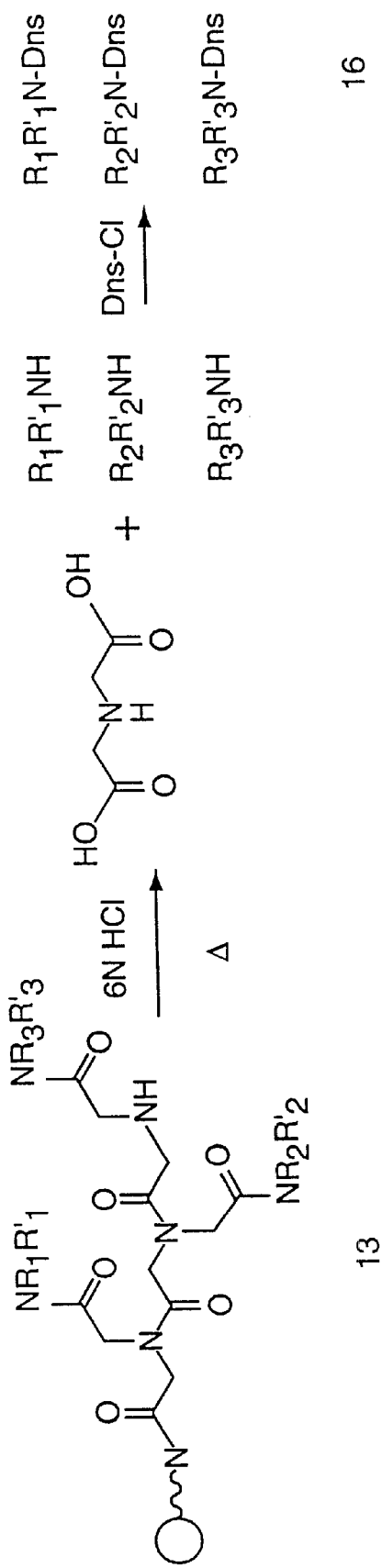

In a preferred embodiment, the protected amino group of amide 12 provides a site for further amide formation for coupling of the next tag resulting in a polyamide comprising n amide units where n corresponds to the number of encryptions employed. The result of such an embodiment is a polyamide which, when n is equal to 3, provides for a triamide such as triamide 13 as illustrated in FIG. 4. In triamide 13, the population of the individual —$NR_1R_1'$, —$NR_2R_2'$ and —$NR_3R_3'$ amines forming each amide define the tags for the first, second and third reaction employed in the synthesis of the target compound.

After compound synthesis, the structure of the compound on the solid support is determined by deencryption of the tags coupled to the supports by measuring that unique property of all of the amine compounds which identify the particular tags employed which, in turn, will identify the reactions employed. Deencryption can be conducted with the tags still coupled to the support or by cleaving the tags from the support. Examples of the first embodiment include amine tags 11 each having a unique $^{13}C$ label on one of the hydrocarbyl groups of the amine but otherwise identical can be identified by, for example, high-resolution gel phase $^{13}C$ nuclear magnetic resonance (NMR) spectroscopy. The high population of $^{13}C$ coupled with its downfield shift in $^{13}C$-nmr would identify of the amine compounds coupled to the support and, hence, the specific tags employed. Moreover, $^{13}C$-NMR spectroscopy can be easily conducted using this technique with little interference from solvent or other non-labeled sites. Solid supports which do not have absorbances in the regions of interest should be used. Suitable supports for this use include those illustrated in FIGS. 9B–9D attached. Preferably, a polystyrene resin, such as TentaGel, or a polyethyleneglycol (PEG) linker, is used. Polystyrene resins tend to be $^{13}$C-invisible and the linker often will exhibit a single sharp resonance at about 70 ppm. This approach is limited, however, because the sensitivity of $^{13}$C-n.m.r. is not sufficient to permit analysis at the level of a single bead unless the bead is very large.

Alternatively, each amine compound used in the binary code format can contain a unique reaction site which can be detected in situ on the support by appropriate reaction thereto. In this embodiment, each amine tag member may comprise, for example, a particular hapten for a labeled monoclonal antibody. Formation of the antibody/hapten pair on the surface of the solid support can be detected by a unique label attached to each antibody.

Preferably, however, the tags are removed from the solid support prior to detection. Such is readily achieved by use of a cleavable linker to attach the tag to the support or by use of standard chemical reactions to chemically decouple the tags from the support. This latter embodiment is illustrated in FIG. 4 wherein the polyamide tag on solid support 13 is treated with 6N HCl to hydrolyze the amide bonds thereby providing for amine tags 15 and iminodiacetic acid 14.

Detection of the amine tags 15 recovered in the reaction solution provides the necessary information as it relates to the compound structure. The particular detection method employed is not critical. However, in one preferred embodiment, these amine compounds are converted to a fluorescent derivative such as dansyl derivative 16 and are then detected by HPLC using a fluorescent detector. Reaction with dansyl chloride to form the fluorescent sulfonamide derivative is particularly preferred in that these derivatives have detection limits at the several femtomoles level. Other suitable fluorescent derivatives include, by way of example, 6-aminoquinolyl-N-hydroxylsuccinimidyl carbamate available from MILLIPORE-ACC.Q. FLUOR Reagent™. In another embodiment, the amine compounds are detected by reaction of the amine compounds with pentafluorobenzoyl chloride to convert the amine to the perfluorobenzyl amide which is then detected by, for example, GC/MS. This method also permits detection at the femtomoles level.

Other embodiments for tagging solid supports with the amine compounds of formula I include those where amine tag synthesis takes place on the solid support. For example, the anhydride can be contacted with a solid support containing amino functionality (e.g., amino acids bound to the solid support through the carboxyl group). The amino functionality opens the anhydride to provide for the amide/acid wherein the carboxyl group is now available for coupling to the binary amine mixture through its activated ester form to provide for a tag of formula I above. It is noted that this tag synthesis strategy provides for the solid supports having the same tag structure as set forth above.

In this embodiment, when a binary mixture of amines is employed to generate the tag in situ, it is common for some amines to be less reactive than the other amines. In order to compensate for these differences in reactivity, the molar amount of the less reactive amines is increased to permit incorporation of these amines into the resulting amide mixture. Ideally, the increase in relative molar amounts is proportional to the relative decrease in the kinetics for a particular amine as compared to the other amine or amines in the binary mixture. Contrarily, when the tags are preformed in the manner of FIG. 1, the difference in the relative kinetics of the reaction of the activated esters of these tags to the solid support or the scaffold is typically not as large and, hence, there is less need to compensate for such differences. However, if the kinetic differences dictate, compensation by virtue of the relative molar amounts of the different amines used in the binary code combination can be used.

Another embodiment for tagging solid supports with the amine compounds of formula I includes those where a carboxyl group on solid support is coupled to the amine moiety of formula I by first protecting the carboxyl group in formula I with a protecting group orthogonal to that employed with the amine functionality followed by differentially deprotecting the amine group and coupling the free amine to the solid support via an amide bond. Subsequent tags are incorporated onto the first tag via removal of the carboxyl protecting group of the first tag and coupling to the amine group of the second tag. It is understood, of course, that hydrolysis of this polyamide with, e.g., 6N HCl, will provide for the same amine tags and iminodiacetic acid obtained in FIG. 4 above.

In still another alternative embodiment, each of the amine tags is independently attached to the solid support either through the amine or carboxyl functionality of these tags. with the remaining functionality remaining blocked. In this embodiment, a percentage of the reactive functionalities on the solid support are reacted with a compound coupling reagent and the remainder of the reactive functionaiities are blocked with an orthogonal blocking group such a photo-labile group (e.g., methylnitropiperonyloxycarbonyl (Menpoc), methylnitropiperonyl (Menp), nitroveratryl (Nv), nitroveratryloxycarbonyl (Nvoc), or nitroveratryloxymethyl ether (Nvom)). Such protecting groups and techniques are described in U.S. Pat. No. 5,148,854 and co-pending U.S. patent applications Ser. No. 07/624,120 filed Dec. 6, 1990, and Ser. No. 07/971,181, filed Nov. 2, 1992 each of which is incorporated herein by reference in its entirety. At each stage of tag coupling, only a fraction of the photolabile protecting groups are removed. Preferably, this fraction is represented by y/n where y represents the total number of photolabile protecting groups on the surface of the resin and n represents the total number of monomer addition steps in the compound synthetic scheme. Coupling of the tag to the fraction of exposed functional groups avoids the necessity for polymer formation because additional functional groups remain available for subsequent tagging. Additionally, in the case where the exposed functional. group on the support is an amino group, this approach permits the use of Br—CH$_2$C(O)NRR' binary tag mixtures to couple to the solid support since reaction of the bromo group with the amino group provides coupling via a —CH$_2$C(O)NRR' group. Acid hydrolysis of the amide yields a solution containing the HNRR' tag for detection in the manner described above.

In still another embodiment, a percentage of the reactive functionalities on the solid support are reacted with a compound coupling reagent and a first tag coupling reagent as above. The remainder of the reactive functionalities are blocked by a number of different orthogonal blocking groups which number corresponds to the number of monomer addition steps employed for compound synthesis. In each subsequent monomer addition step, a different orthogonal blocking group is removed and the exposed reactive functionality employed to couple the amine tag. Again, this approach does not require the formation of a polyamide but, upon deprotection and hydrolysis of the resin with e.g., 6N HCl, the resulting amines are identical to amine tags 15 and iminodiacetic acid 14 obtained in FIG. 4 above.

IV. TERNARY CODES

While binary code formats set forth above provide a means to encrypt the structure of target compounds, ternary or higher codes provide a means to encrypt the same amount of information using fewer amine compounds. Ternary codes can be based on, for example, chemical identity and the presence of a compound at two different concentrations.[16] In this case, the three states defining the ternary code would be the presence of the compound at two different and distinguishable concentrations or its absence. The advantage of higher order codes over a binary code is that fewer compounds are required to encode the same quantity of information about the synthesis or, using the same number of compounds, more information can be encoded.

When employing different amines at different concentrations for a ternary or higher code, care must be taken to ensure that the different amines possess similar reactivity so that the amount incorporated is predictable. One means for obviating this concern is to employ the same amine having different levels of isotopic incorporation (e.g., $^2H$, $^{13}C$, etc.). In this embodiment, the amines possess identical reactivity and the relative levels of isotopic incorporation can be detected via mass spectroscopy of the cleaved products.

V. UTILITY

The hard tagging methods described above are useful for encrypting the structure of a target compound formed on the surface of solid support and has particularly utility in combinatorial chemistry. Specifically, in combinatorial chemistry, libraries of target compounds are prepared on solid supports wherein each support contains multiple copies of a single target compound which are obtained via the efficient "split/pool" method to assemble all possible combinations of a set of chemical building blocks.[3]

The most efficient use of the resulting combinatorial libraries is to screen the entire library for interaction with macromolecular receptors either in binding assays where the target compounds remain tethered to their synthetic supports, or in soluble assays after cleavage of the target compounds from the resin., In either case, the elucidation of the chemical structure for the library is limited only to those members having biological activity in the screen. The encryption methods described herein are particularly suited for such structural elucidation. As an example, the use of 130 μm diameter TENTAGEL S resin, a standard polystyrene-polyethyleneglycol graft copolymer available from Rappe Polymere with a loading of ~300 pmoles $NH_2$/bead with approximately 10% of these amino groups dedicated for tag addition, leaves ~270 pmoles/bead of amino functionality for target compound synthesis. Accordingly, after target compound synthesis, cleavage of the compound from the bead into a volume of 100 μL in a microtiter well would yield an adequate concentration of target compound for biological assay (i.e., ~2.7 μM). If the target compound is active, then the structure of that compound can be elucidated from the tags coupled to the solid support.

One preferred method for screening an encoded library prepared in this manner involves target compound coupling to the solid support via a photolabile linker, distribution of single resin beads into individual wells of microtiter plates for ligand photocleavage and assay. Photocleavage releases the target compound into the assay medium free of byproducts, leaving the tag moieties covalently attached to the beads. After identification of wells having target compounds with biological activity, the corresponding beads are recovered for tag analysis and thus compound determination.

Some of the features of the tags described herein include one or more of the following: a) the tag entity is easily detached from the solid support by using reliable known methods; b) detection limit for the tags are very low; c) reaction conditions for attaching the tags to the solid supports are mild enough not to affect the synthesis of the compound; d) the tags are stable under various reaction conditions; and e) can be easily synthesized in large quantity and in large scale.

EXAMPLES

The following examples are set forth to illustrate the claimed invention and are not to be construed as a limitation thereof.

Unless otherwise stated, all temperatures are in degrees Celsius. Also, in these examples, unless otherwise defined below, the abbreviations employed have their generally accepted meaning:

| | |
|---|---|
| Alloc = | allyloxycarbonyl |
| Boc = | tert-butyl oxycarbonyl |
| BOP = | benzotriazol-1-yloxytris(dimethylamino) phosphonium hexafluorophosphate |
| DCC = | dicyclohexylcarbodiimide |
| DCM = | dichloromethane |
| DIC = | 1,3-diisopropylcarbodiimide |
| DIEA = | diisopropylethylamine |
| DMAP = | p-dimethylaminopyridine |
| DMF = | N,N-dimethylformamide |
| Fmoc = | fluorenylmethyl oxycarbonyl |
| g = | gram |
| $^1$H-nmr = | proton nuclear magnetic resonance |
| HATU = | O-(7-azabenzotrizol-1-yl)-1,1,3,3-tetramethyluronium hexafluorophosphate |
| HBTU = | 2-(1H-benzotriazol-1-yl)-1,1,3,3-tetramethyluronium hexafluorophosphate |
| HOBT = | 1,hydroxybenzotrizole |
| HPLC = | high performance liquid chromatography |
| M = | molar |
| mg = | milligram |
| mL = | milliliter |
| mM = | millimolar |
| mmol = | millimol |
| N = | normal |
| Pfp = | pentafluorophenyl |
| Su = | succinyl |
| TBAF = | tetrabutylammonium fluoride |
| $TMSN_3$ = | azidotrimethylsilane |
| TFA = | trifluoroacetic acid |
| THF = | tetrahydrofuran |
| μL = | microliters |
| μm = | micron |

Additionally the Sasrin resin described herein is commercially available from Bachem Biosciences and the TENTAGEL AC and TENTAGEL PHB, each of which is a polystyrene-polyethyleneglycol graft copolymer, with a benzylic hydroxyl synthesis handle and TENTAGEL RAM resin, a polystyrene-polyethyleneglycol graft copolymer with a NH-FMOC synthesis handle are commercially available from Rapp Polymere, Tubigen, Germany. Each of these resins is depicted in FIGS. 9A–9D respectively. In the Examples listed below, several commercially available reagents are listed by company name as follows:

Aldrich=Aldrich Chemical Company, Milwaukee, Wis., USA

Rapp Polymere=Rapp Polymere, Tubingen, Germany

Advanced ChemTech=Advanced ChemTech, Louisville, Ky., USA

Millipore=Millipore, Milford, Mass., USA

Example 1

This example exemplifies general methods for the synthesis of amine tags for use in this invention. The synthetic methods employed in this example are set forth below as well as in FIG. 1.

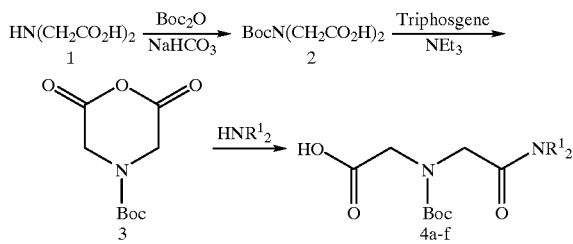

Reagents

Iminodiacetic acid (Aldrich), 5.0 g

Di-tert-butyl dicarbonate (Aldrich), 9.85 g

THF (Aldrich), 50 mL

Triethylamine (Aldrich), 2.43 g

Triphosgene (Aldrich), 0.84 g

Sodium bicarbonate, 12.6 g

Ethyl acetate

To a solution of iminodiacetic acid 1 in 100 mL of THF and water (1:1) was slowly added sodium bicarbonate. After 10 minutes, di-tert-butyl dicarbonate was added. The solution was stirred for 2 days. After the THF was removed, the aqueous layer was extracted with ether twice, and acidified with 6N HCl (30 mL) to pH 1, extracted with ethyl acetate. The organic layers were washed with brine, dried over sodium sulfate and concentrated to give 8.1 g (92%) of Boc-diacid 2 which was recrystallized from hot ethyl acetate.

To a solution of 2.0 g of Boc-diacid 2 in 100 mL of ethyl acetate at 0° C. was added triethylamine and powdered triphosgene. The mixture was stirred at 0° C. for 15 minutes and at room temperature for 15 minutes, and washed with brine, 0.1 N HCl, aqueous sodium bicarbonate (5%), and brine. The solution was dried over magnesium sulfate and concentrated to give a solid, which was recrystallized with ether to give 1.41 g (76%) of anhydride 3 as a white crystalline solid.

B. Preparation of Tags 4 from Boc-Anhydride and Amines

Reagents

Dioctylamine, 4.22 mL

Ethyl acetate

To a solution of Boc-anhydride 3 (3.0 g) in 50 mL of ethyl acetate at room temperature was added dioctylamine in one portion. The solution was stirred overnight and concentrated to give a residue, which was subjected to column chromatography on silica gel eluting with 10% hexane in ethyl acetate to give 3.2 g (77%) of dioctyl tag 4f as a white solid.

Other tags 4a–4e were prepared in a similar fashion in good yields.

Likewise, the Boc protecting group can be replaced with other compatible protecting groups such as an Alloc protecting group. In this case, the alloc protected tags are formed by contacting allyloxycarbonyl chloride and iminodiacetic acid in 50% dioxane and sodium bicarbonate. Anhydride formation and subsequent formation of tags using the Alloc protecting group follows the procedures set forth above. Alloc removal can be accomplished by adding the alloc-protected amino resin (0.1 mmol, ~0.25 mmol/g) to a solution tetrakis(triphenylphosphine)palladium(0) (0.023 g, 0.02 mmol) in DCM (2 mL). A solution of tetrabutylammonium fluoride (0.078 g, 0.3 mmol) and azidotrimethylsilane (0.106 mL, 0.092 g, 0.8 mmol) in DCM (2 mL) is prepared and allowed to stand at room temperature for 5 minutes before addition to the resin mixture. The mixture is flushed with nitrogen and gently shaken. After 30 minutes the mixture is drained, and the resin washed with DCM (2×5 mL). The deprotection procedure is then repeated. The resin is subsequently treated with a 3% w/v solution of sodium diethyldithiocarbamate in N-methyl pyrrolidone containing 5% v/v diisopropylethylamine (5 mL). After shaking for 10 minutes the mixture is drained, and the resin washed with N-methyl pyrrolidone (3×5 mL).

Coupling of a mixture of Alloc-protected tag monomers to the resin can then be achieved using HATU according to the protocol described above.

Example 2

This example exemplifies formation of compound coupling sites and tag coupling sites on a solid support. The synthetic methods employed in this example are set forth below as well as in FIG. 1.

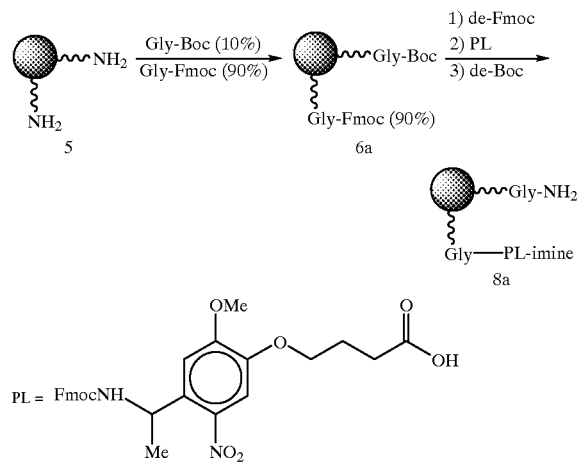

Reagents

TENTAGEL-130, a polystyrene-polyethyleneglycol graft copolymer with a diameter of 130 microns (0.3 mmol/g), (Rapp Polymere), 1.0 g Fmoc-Gly (Advanced ChemTech), 200 mg Boc-Gly (Aldrich), 13 mg HOBT (Advanced ChemTech), 101 mg DIC (Aldrich), 2 mL Pyridine (Aldrich), 2 mL Acetic Anhydride (Aldrich), 2 mL

DMF

Methanol

DCM

HATU (Millipore)

DIEA (Aldrich)

TFA

TENTAGEL beads 5 in a solid phase reaction vessel (from ChemGlass, Inc., Vineland, N.J. 08360) were washed with DMF three times. To the beads was added a solution of Fmoc-Gly, Boc-Gly, HOBT and DIC in 3 mL of DMF. The beads were shaken for 3 hours and washed with DMF three times. Pyridine and acetic anhydride were added to cap the free amino groups. After 10 minutes, the beads were washed with DMF, methanol and DCM three times each and dried under vacuum.

A portion of the beads (0.4 g) was washed with DMF three times to provide for beads 6a having amine groups orthogonally blocked on the surface of the bead. To beads 6a was added a solution of piperidine in DMF (20%, 2 mL). After 30 minutes, the beads were washed with DMF, methanol, and DMF three times each. A solution of photolinker (PL) (187 mg, 0.36 mmol), HATU (137 mg, 0.36 mmol) and DIEA (60 1L) in DMF (0.6 mL) was added. After 20 minutes, the beads were washed with DMF, methanol, and DCM three times each. To the beads was added a solution of TFA in DCM (50%, 2 mL). The beads were shaken for 30 minutes and washed with DCM three times. DIEA in DCM (50%, 2 mL) was added. After being shaken for 30 minutes, the beads were washed with DCM, methanol, and DCM three times each, and dried under vacuum to provide for beads 8a.

Example 3

Figure 5:
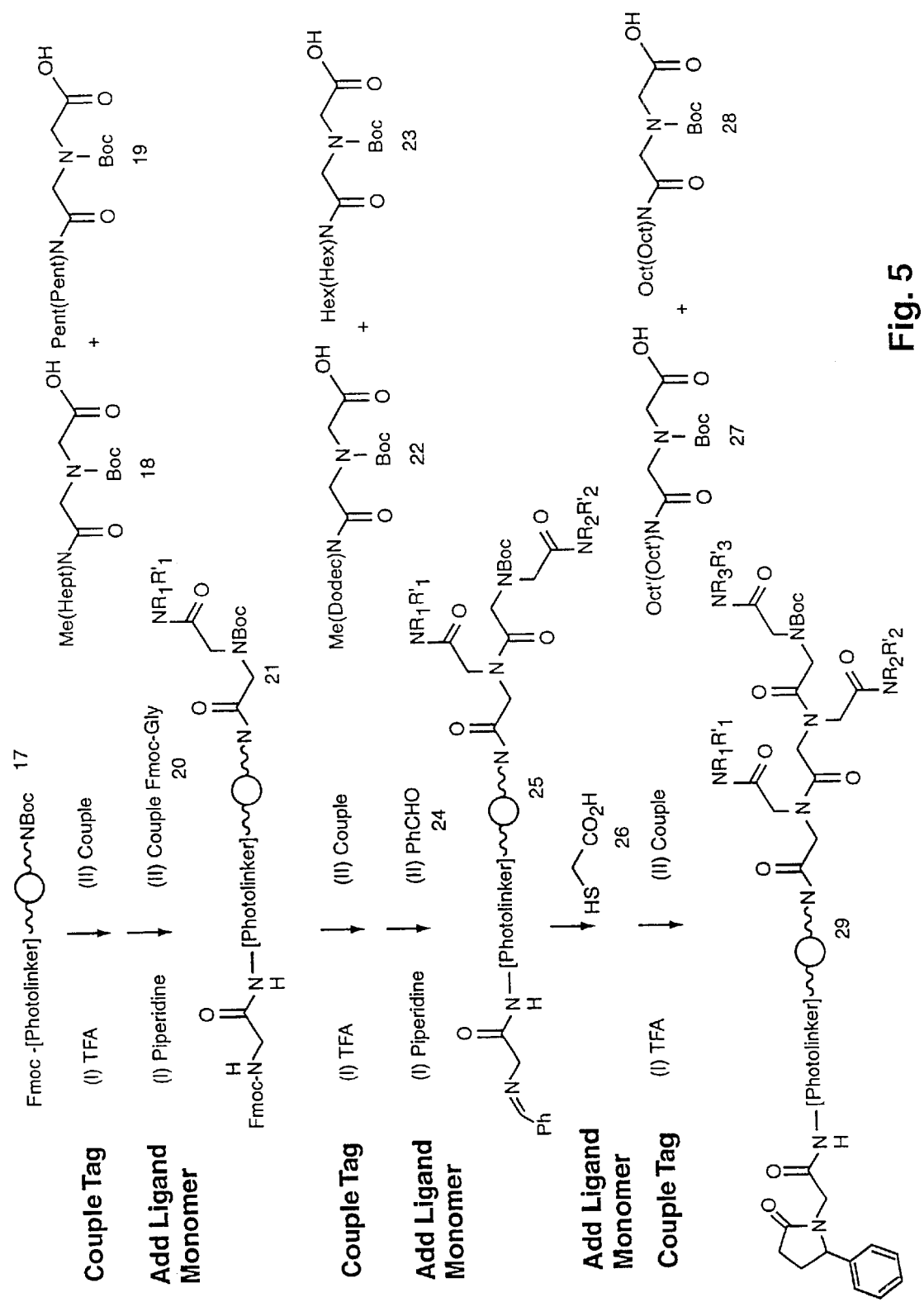
FIG. 5 illustrates the use of amine tags coupled to a solid support to encode the structure of a target thiazolidinone compound formed on the surface of this support.

This example exemplifies the formation of a single encoded thiazolidinone compound on a solid support. This example demonstrates that encoded libraries of thiazolidinones can be straightforwardly prepared by incorporating resin splitting and pooling cycles at intermediate steps in the synthesis. The synthetic methods employed in this example are set forth below as well as in FIG. 5.

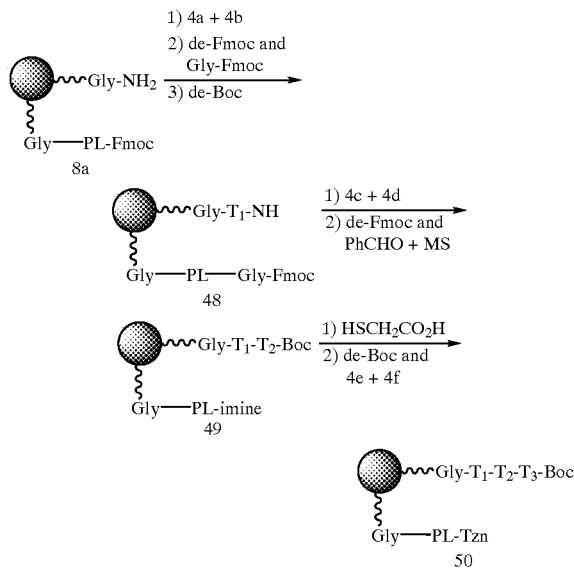

TENTAGEL beads 8a (0.2 g) prepared as above were washed with DMF three times. A solution of tags (La and 4b, 0.18 mmol total) prepared as in Example 1 above, HATU (68 mg) and DIEA (30 µL) in DMF (0.2 mL) was prepared and mixed for 2 minutes before being added to the beads. The beads were shaken for 20 minutes and washed with DMF three times.

Piperidine in DMF (20%, 1 mL) was added to the beads. After 20 minutes, the beads were washed with DMF, methanol, and DMF again three times each. A solution of Fmoc-Gly (54 mg), HATU (68 mg) and DIEA (30 pL) in DMF (0.3 mL) was prepared and mixed for 2 minutes before being added to the beads. After 20 minutes, the beads were washed with DMF, methanol, and DCM three times each.

The cycle of Boc-deprotection, tag coupling (4c and 4d), and Fmoc-deprotection was repeated to give free amine, which was suspended in THF (2 mL). To the beads were added 3A molecular sieves (0.5 g) and benzaldehyde (183 µL). The mixture was heated at 70° C. for 3 hours and the molecular sieves were then removed. The beads were washed with DCM three times to provide for beads 49 which were suspended in THF (2 mL). To the beads were added 3A molecular sieves (0.5 g) and mercaptoacetic acid (100 µL). The mixture was heated at 70° C. for 3 hours and the molecular sieves then removed. The beads were washed with DCM, methanol, and DCM three times each.

The process of Boc-deprotection and tag coupling (4e and At was repeated to give solid support 50 having multiple copies of a single thiazolidinone compound the structure of which is encoded by amine tags 4a–4f bound to the solid support as a polyamide.

Note that the order of tag and monomer additions is switched between the second and third steps of the synthesis. This strategy prevented unnecessary manipulation of the potentially labile benzylidine imine intermediate.

The thiazolidinone compound could be cleaved photolytically for bio-assay. The bead was decoded by hydrolysis of the tag amides and subsequent dansyl chloride derivatization for HPLC detection using a fluorescent detector. Specific procedures for decoupling and dansylating the amine tags are as follows:

A single bead (before or after compound removal) was placed in a capillary tube. After 0.1 mL of 6 N HCl was added, the capillary was sealed and heated on a heating block at 130° to 140° C. for 15 hours. The tube was opened and excess HCl was removed by lyophilization. To the tube was added 40 µL of aqueous lithium carbonate (40 mg in 10 mL of water, 0.054 M) and 40 µL of acetonitrile. After mixing for 10 minutes, 40 µL of dansyl chloride solution (2 mg in 10 mL of acetonitrile, 0.074 mM) was added. The mixture was agitated for 10 minutes, diluted to 1.0 mL with acetonitrile and filtered through a 4 µm filter. The tag solution (20 µL) was injected onto a reversed phase HPLC column for analysis.

The following set of chromatographic and detection conditions are used with a Beckman System Gold instrument to separate and to detect individual dansyl amides.

| | |
|---|---|
| Column: | Alltech Adsorbosphere Narrow-Bore C18 Solvent Miser column (5 microns) with 2.1 mm in diameter and 250 mm in length. |
| Eluents: | Eluent A: 50 mM NH$_4$OAc aqueous solution with pH at 7.5 adjusted by adding acetic acid or ammonium hydroxide |
| | Eluent B: 2% of eluent A in acetonitrile |
| Gradient: | 65% eluent B for 1 minute |
| | 65% to 100% eluent B over 10 minutes with curve 3 |
| | 100% eluent B for 24 minutes |
| Flow rate: | 0.25 mL/minute |

Fluorescent Detector: Shimadzu Fluorescence HPLC monitor (Model RT-551) with excitation wavelength at 352 nm, emission wavelength at 510 nm and sensitivity at high level. The fluorescence detector is relayed to the HPLC system through a Beckman Analog Interface Module (Model 406).

Figure 6:
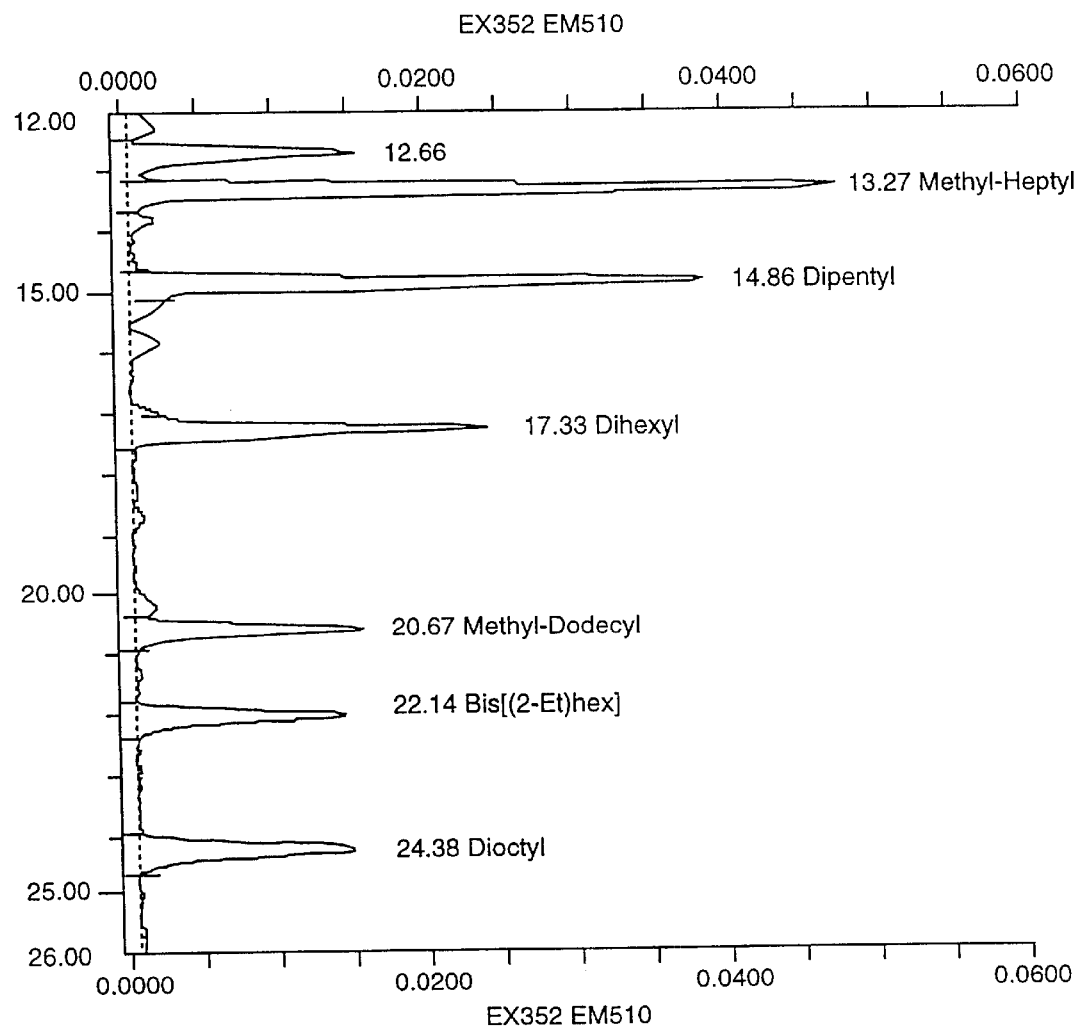
FIG. 6 illustrates deencryption of this structure from the amine tags of FIG. 5 to identify the structure of the target thiazolidinone compound.
Figure 7A:
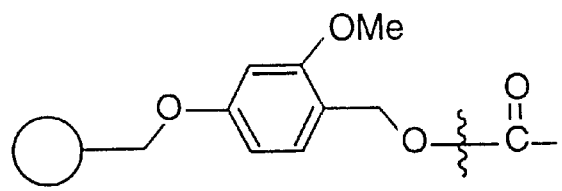
FIGS. 7A–7D illustrates several cleavable linking arms for covalently linking amine compounds to the solid support.
Figure 7B:
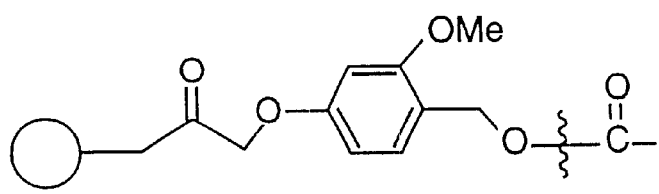
Figure 7C:
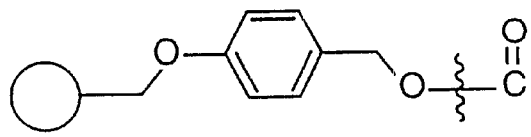
Figure 7D:
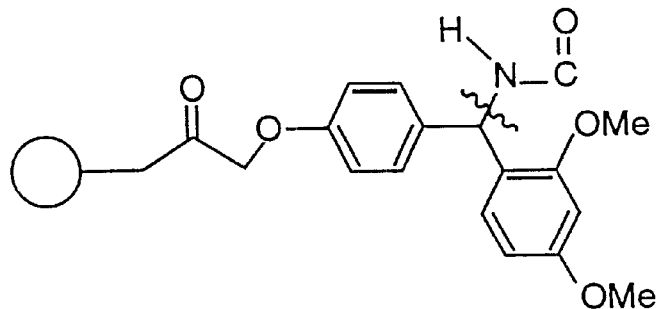

FIG. 6 illustrates the presence of all 6 amines in the HPLC trace.

Since the fluorescence detection threshold for these dansyl sulfonamides is typically 20–30 fmoles, there is more than sufficient tags available form a single bead for unambiguous analysis. Indeed, generally only 2–5% of the dansylated hydrolysate from an individual bead is injected onto the HPLC column.

Example 4

This example exemplifies the formation of a single encoded β-lactam compound on a solid support. The synthetic methods employed in this example are set forth below:

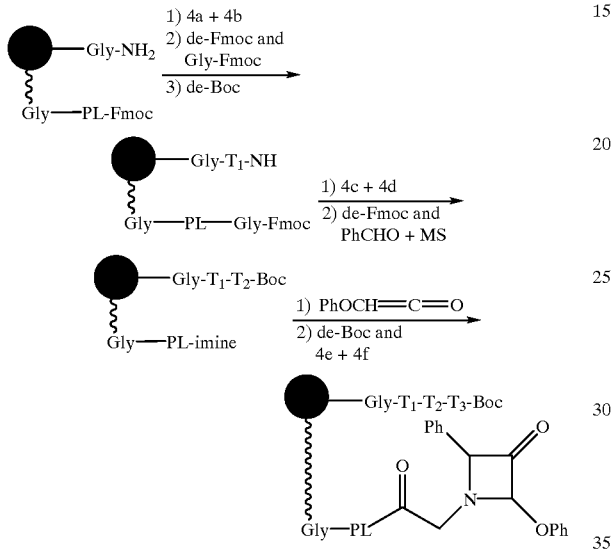

The experimental procedures for the formation of the imine and the corresponding tagging in the synthesis of the β-lactam are the same as those set forth above for the synthesis of the thiazolidinone in Example 3.

To the tagged imine beads in DCM (2 mL) was added triethylamine and the mixture was cooled to −78° C. under a nitrogen atmosphere. 2-phenyloxy acetyl chloride was added, and the mixture was allowed to warm to room temperature. After 15 hours, the beads were washed with DCM, methanol and DCM three times each.

The process of Boc-deprotection and tag coupling (4e and 4) was repeated to give encode β-lactam.

The β-lactam compound could be cleaved photolytically for bio-assay and the bead was decoded by hydrolysis of the tag amides and subsequent dansyl chloride derivatization for HPLC detection using a fluorescent detector. Encoded libraries of β-lactams can, accordingly, be straightforwardly prepared by incorporating resin splitting and pooling cycles at intermediate steps in the synthesis.

Example 5

This example exemplifies the formation of a 7×7×7 encoded thiazolidinone compound on a solid support. The synthetic methods employed in this example are set forth below:

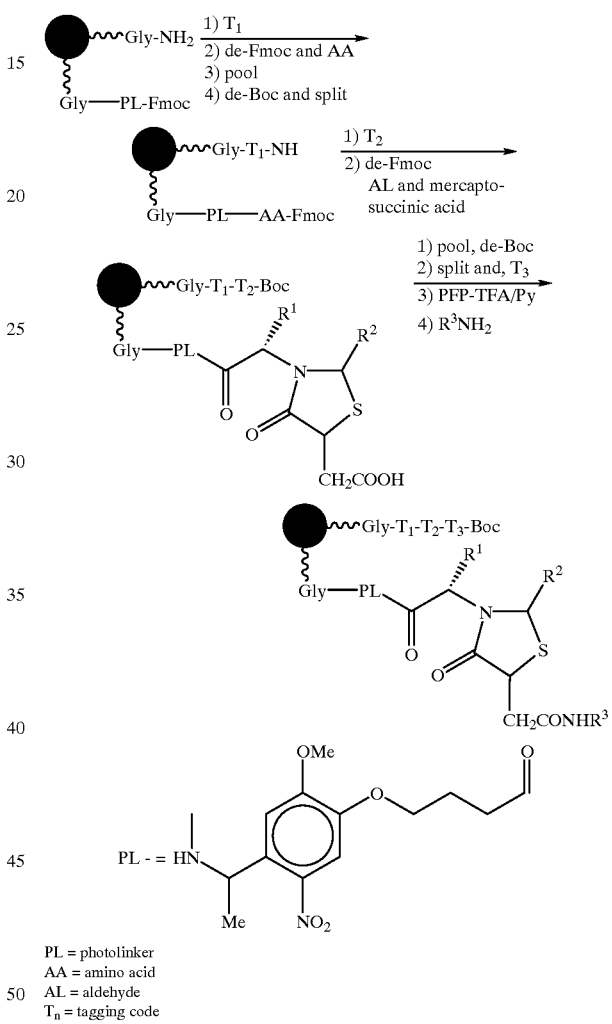

PL = photolinker
AA = amino acid
AL = aldehyde
$T_n$ = tagging code

TABLE 1

Tags and Building Blocks

| $T_1$ | AA | $T_2$ | RCHO | $T_3$ | Amine |
|---|---|---|---|---|---|
| BP | Gly | MD | Ph | BB' | A1 |
| PP | cHA | O'O' | 3-Py | MH | A2 |
| HH | Phe | OO | 2-Cl—Ph | MH' | A3 |
| BP + PP | 3-PyA | MD + O'O' | c-Hex | BB' + MH | A4 |
| BP + HH | h-Phe | MD + OO | 3-AcOPh | BB' + MH' | A5 |
| PP + HH | β-Nap | O'O' + OO | $Ph(CH_2)_2$ | MH + MH' | A6 |
| BP + PP + HH | D-Ala | MD + O'O' + OO | 4-AcOPh | BB' + MH + MH' | A7 |

TABLE 1-continued

Tags and Building Blocks

| $T_1$ | AA | $T_2$ | RCHO | $T_3$ | Amine |
|---|---|---|---|---|---|

$R_1R_2$ in the tags: BP=butylpentyl; PP=dipentyl; HH=dihexyl; MD=methyldodecyl; O'O'=bis[(2-ethyl) hexyl]; OO=dioctyl; BB'=butylbenzyl; MH=methylhexyl; MH'=methylheptyl.

AA (Fmoc protected amino acid): Gly=glycine; cHA=3-(cyclohexyl)alanine; Phe=3-(phenyl)alanine; 3-PyA=3-(3-pyridyl)alanine; h-Phe=3-(homophenyl)alanine; O-Nap=3-(2-naphthyl)alanine; D-Ala=D-alanine A1
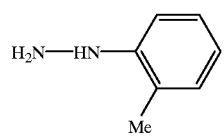

A2
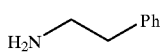

A3
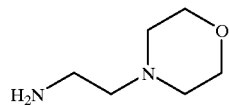

A5
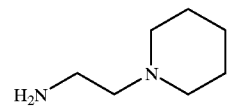

A6
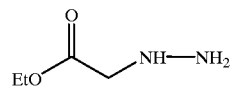

A7
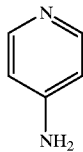

Preparation of Three Sets of Activated Tags ($T_1$, $T_2$ and $T_3$) at Each Step.

Tags (0.18 mmol for one tag, 0.09 mmol each for two tags, and 0.06 mmol each for three tags, for details see Table above) were weighed out'for each pool, and dissolved in 0.2 mL of DMP. To each pool were added 0.2 mL of HATU solution in DMF (0.9 M, 0.18 mmol) and 60 μL of DIEA, and mixed for two minutes before reacting with beads.

Coupling of first Tag ($T_1$) and Coupling of Amino Acid (AA)

Seven pools of differentiated beads (0.2 mg each) were washed with DMP three times, and then treated with first set of tag $T_1$ wherein each $T_1$ tag encodes for a different amino acid (AA) as set forth in the table above. After 20 minutes, the beads were washed with DMF three times. To each pool of beads were added 1 mL of DMF and 1 mL of piperidine. After 20 minutes, the beads were washed with DMF, DCM and DMF two times each. A separate amino acid (0.18 mmol) for each pool was dissolved in 0.2 mL of DMF, and treated with HATU (0.9 M, 0.2 mL) and DIEA (60 82 L) for 2 minutes. The activated amino acids were added to individual pools of beads. After 20 minutes, the beads were washed with DMF three times.

Coupling of Second Tag ($T_2$) and Formation of Thiazolidinone Ring

The seven pools of beads were collected and mixed in a parent vessel and washed with DCM three times, and treated with TFA in DCM (50%, 6 mL) for 30 minutes. The beads were washed with DCM three times and treated with DIEA in DCM (50%, 6 mL) for 30 minutes. The beads were washed with DCM, methanol and DCM three times each, and split into seven portions. The beads were washed with DMF three times and treated with second set of tag(s) ($T_2$) for 15 hours. The beads were washed with DMF three times, and treated with piperidine in DMF (50%, 2 mL) for 20 minutes. After being washed with DMF, methanol, and DCM three times each, the beads were dried under vacuum. To each pool of beads were added 1 mL of THF, 1.0 g of 3A molecular sieves, 0.9 mmol of a different aldehyde as per the above table, and 0.9 mL of mercaptoacetic acid in THF (2 M, 1.8 mmol). The vessels were capped and heated at 70° C. in a water bath for 4 hours. The beads were washed with DMF, methanol and DCM three times each.

Coupling of Third Tags (Td and Formation of Amide

The seven pools of beads were pooled together and washed with DCM, and treated with TFA (50%, 6 mL) for 20 minutes. After being washed with DCM three times, the beads were treated with DIEA (50%, 6 mL) for 20 minutes, and washed with DMF three times, and treated with the third set of tag(s) ($T_3$) for 15 hours. The beads were washed with DMF, methanol and DMF three times each, and a solution of pentafluorophenyl trifluoroacetate (2 M) and pyridine (4 M) in DMF (1.5 mL) were added to the beads. After 30 minutes, the beads were washed with DMF three times, and 6.1 mL of DIEA in DMF (1.0 M) were added. Amine (see table above details) (hydrazide-HCl was treated with the DIEA solution first) was added to the beads. After 30 minutes, the beads were washed with DMF, methanol, and ether three times each, and dried under vacuum.

Biological assays on a solution phase of such thiazolidinones can be conducted by cleaving these compounds from the solid support. Specifically, a single bead from the library is placed in a titer-well and suspended in 100 μL of water in methanol (1:1). The bead is photolyzed for 2 hours on a shaker table using top illumination from a Mercury Arc lamp equipped with a 350–450 nm dichroic reflector with a measured power level of 10 mW/cm² at 365 nm. The resulting solution phase of the particular thiazolidinone is assayed for biological activity. Those wells exhibiting such activity are then treated with 6N HCL and analyzed on HPLC as described above in order to determine the structure of the active thiazolidinone.

Example 6

The purpose of this example is to illustrate that relative differences in the reaction kinetics of different amines can be compensated for by adjusting the molar amounts of these amines. This example employs the following reaction scheme:

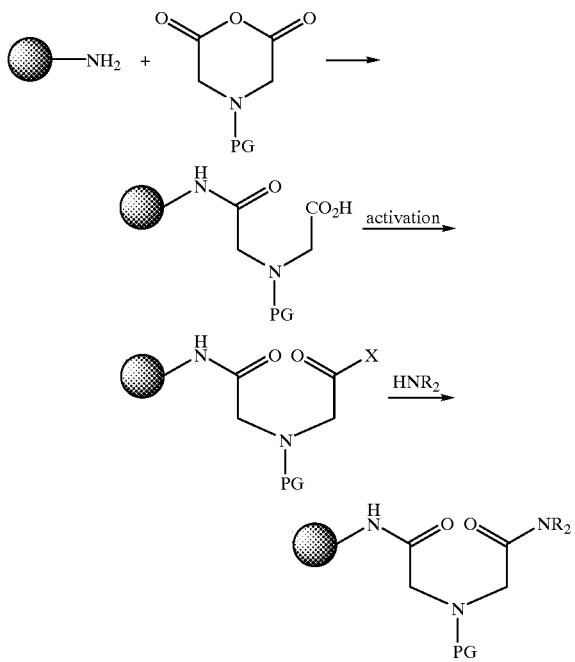

PG = Boc, Fmoc, Alloc, etc.
R = Butyl, Hexyl, Octyl, etc.

Specifically, the anhydride formed in the manner described above was ring opened by reaction with a solid support having amino functionalities to provide for the amide acid. Activation of the carboxylic acid with PfpO$_2$CCF$_3$ was followed by amidation with a binary amine mixture acting as the tag and the resulting product profile analyzed. Systematic variation in the molar ratios allowed reactivity coefficients for each amine to be calculated. The results of this analysis are reported in the table below:

| Amine | Ratio of Amines in Amine Mixture | Ratio of Amine in Product | Ratio of Amines in Amine Mixture | Ratio of Amine in Product |
|---|---|---|---|---|
| Bu$_2$NH | 1.0 | 1.0 | 1.0 | 1.0 |
| Pent$_2$NH | 1.0 | 0.70 | 1.2 | 0.88 |
| Hex$_2$NH | 1.0 | 0.62 | 1.4 | 0.98 |
| Oc$_2$NH | 1.0 | 0.37 | 1.6 | 0.87 |

Bu = n-butyl
Pent = n-pentyl
Hex = n-hexyl
Oc = n-octyl

These results suggest one means for compensating for the different reaction kinetics of different amines in a binary amine mixture acting as a tag. Alternatively, if the relative reaction rates of the amines are known or determined, the subsets of binary amine mixtures from the tag pool can be selected to provide relatively equal reaction rates. Thus, from a pool of 12 amines, if 4 possess relatively high reaction rates, 4 amines possess relatively moderate reaction rates and 4 amines possess relatively low reaction rates, the three subsets of tags used in 3 step synthesis would preferably include those amines having relatively equal reaction rates.

Example 7

In order to accommodate more tags for large libraries, several HPLC conditions were explored. Two sets of HPLC conditions were especially suitable for both a short run, using relatively small numbers of tags (7~9 tags) and a long run using relatively large numbers of tags (~15 tags). The column used in both cases was an Absorbosphere Narrowbore C$_{18}$ solvent miser column having a 2.1 mm diameter, 250 mm length (available from Alltech, Deerfield, Ill. 60015).

In the short run, the eluants employed were:

A: 50 mmol NH$_4$Ac (in water)
B: 2% of A in acetonitrile

| | Gradients: | | | |
|---|---|---|---|---|
| Time | A | B | Duration | Curve |
| Init. | 35 | 65 | | |
| 1 | 0 | 100 | 10 | 3 |
| 25 | 35 | 65 | | |
| 30 | 35 | 65 | | end |

In the long run, the eluants employed were:

A: H$_2$O
B: acetonitrile

| | Gradients: | | | |
|---|---|---|---|---|
| Time | A | B | Duration | Curve |
| Init. | 45 | 55 | | |
| 1 | 41 | 59 | 5 | 0 |
| 5 | 0 | 100 | 49 | |
| 60 | 45 | 55 | | |
| 65 | 45 | 55 | | end |

Tables of retention times for the dansylated derivatives of these amines are shown below:

Retention Time for Shorter Run

| Amine Used to Prepare Sulfonamide | Retention Time |
|---|---|
| butylbenzylamine | 10.98 minutes |
| methylhexylamine | 11.33 minutes |
| dibutylamine | 11.86 minutes |
| heptylmethylamine | 12.79 minutes |
| amylbutylamine | 13.45 minutes |
| dipentylamine | 15.05 minutes |
| dihexylamine | 18.27 minutes |
| bis(2-ethylhexyl)amine | 25.43 minutes |
| dioctylamine | 28.25 minutes |

| Retention Time for Longer Run | |
| --- | --- |
| Amine Used to Prepare Sulfonamide | Retention Time |
| morpholine | 7.03 minutes |
| bis(2-methylethyl)amine | 8.46 minutes |
| pyrrolidine | 10.08 minutes |
| piperidine | 14.45 minutes |
| tetrahydroisoquinoline | 17.94 minutes |
| ethylbenzylamine | 19.60 minutes |
| butylethyleamine | 19.82 minutes |
| methylhexylamine | 26.07 minutes |
| butylbenzylamine | 27.36 minutes |
| dibenzylamine | 27.46 minutes |
| 4-benzylpiperidine | 27.49 minutes |
| dibutylamine | 28.39 minutes |
| benzyl-2-phenethylamine | 29.10 minutes |
| heptylmethylamine | 30.98 minutes |
| amylbutylamine | 33.01 minutes |
| (9-methylaminomethyl)-anthracene | 33.66 minutes |
| dipentylamine | 37.41 minutes |
| dihexylamine | 45.80 minutes |
| bis(2-ethylhexyl)amine | 55.57 minutes |
| dioctylamine | 58.47 minutes |

The relative retention times of sulfonamides on HPLC varied slightly from one run to another depending on the pre-equilibrium of the column. A new column usually gave better resolution and longer retention times for tags with long retention time. This kind of variations of retention time is easily corrected with a standard solution of known tags.

From the HPLC retention time table (second Table), it is easy to find that these peaes were spreading between 10 and 60 minutes range. This data indicates that a variety of different amines are distinguishable from each other based on HPLC data. Additionally, there are several time intervals available, which permits additional amines, as their appropriate dansyl amides, to be used.

Based on the criteria for choosing amines for tagging and subsequent fluorescent detection as their dansyl sulfonamide derivative, these secondary amines must have sufficient reactivity with dansyl chloride. Most of these amines are long chain amines with different chain lengths, which resulted in the separation on HPLC. Although commercially available amines meeting these criteria are limited, there are more than 10 amines resolvable on HPLC. Additionally, the literature is replete with methods for preparing suitable secondary amines. For example, reductive amination to synthesize secondary amines uses a primary amine and an aldehyde to form an imine, followed by reduction. Imine formation is carried out in dichloromethane at room temperature using a dehydrating agent such as molecular sieves, magnesium sulfate. After formation, the imine is immediately reduced to the secondary amine with, e.g., sodium borohydride.

Example 8

This example illustrates the synthesis of a 4 (amino acids)×4 (aldehydes)×5 (olefins)×3 (acid chlorides) encoded pyrrolidinone library on a solid support which requires 3+3+3+2 tags or a total of eleven tags. The synthetic methods employed in this example are set forth in FIGS. 8–10.

Figure 9:
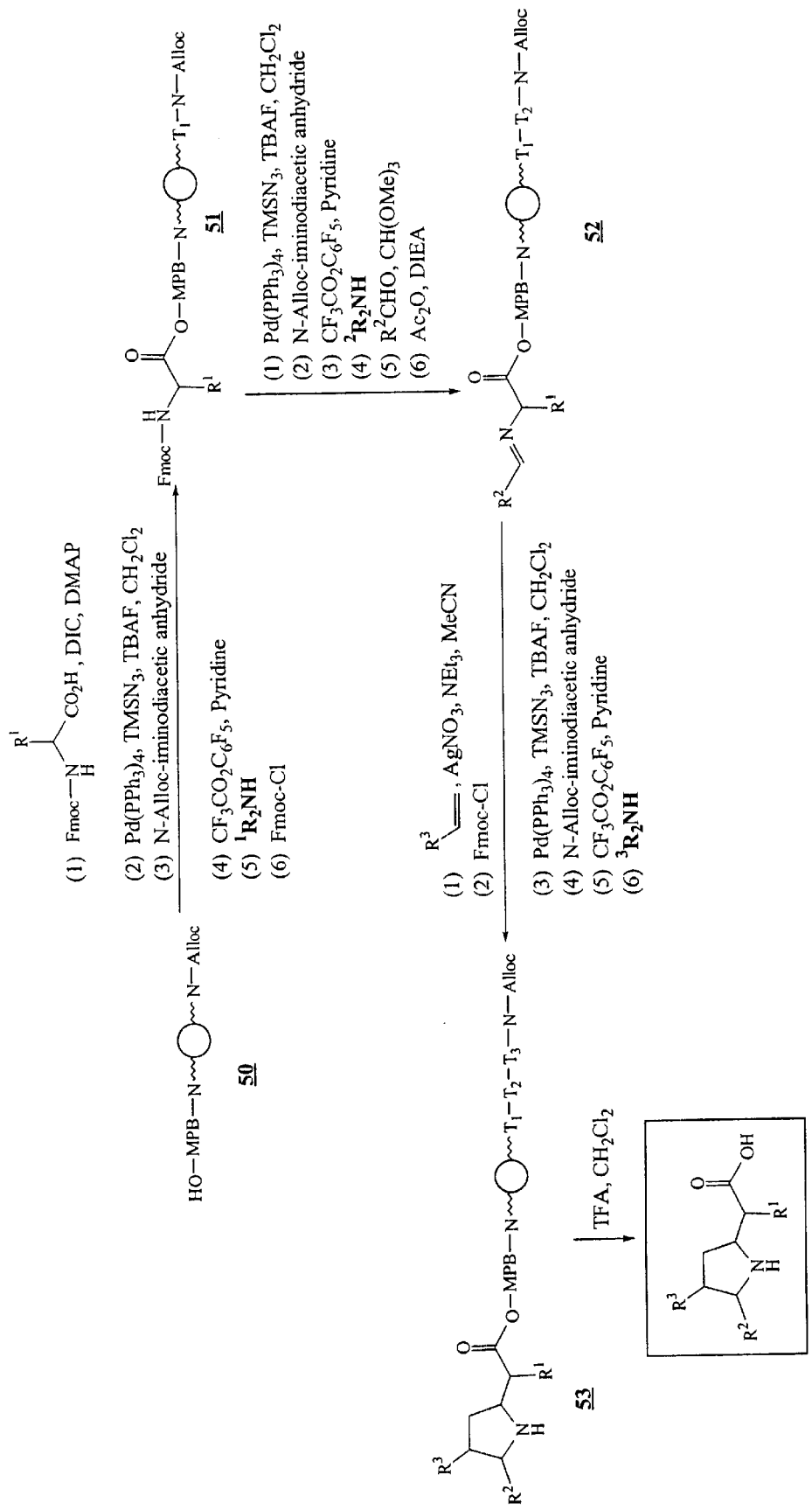

In FIG. 9, the term MPB refers to

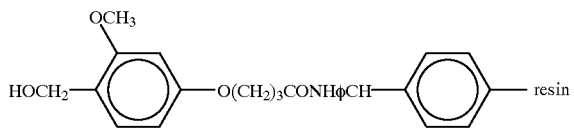

FIG. 9 illustrates the synthetic steps employed in the solid phase preparation of pyrrolidines. Specifically, resin 50 (made by conventional methods from resins available from Novo Biochem, La Jolla, Calif., 92039) was treated by conventional means to attach an Fmoc protected amino acid to the HO—MPB—N group followed by removal of the Alloc protecting group with Pd(PPh$_3$)$_4$, TMSN$_3$, TBAF in methylene chloride to provide for the free amine. Coupling of an N-Alloc-iminodiacetic anhydride group opens the anhydride to the amidelacid wherein the acid group is activated via CF$_3$CO$_2$C$_6$F$_5$ and pyridine and then converted to the amide via reaction with the first amine tag represented as either $^1$R$_2$NH or T$_1$. Insofar as the reaction removes the Fmoc protecting group on the amino acid, this group is then reprotected via reaction with Fmoc-Cl to provide for compound 51.

The Alloc group of compound 51 is removed as above and a second tag $^2$R$_2$NH (T$_2$) is incorporated onto the structure which also removes the Fmoc group. After tag incorporation, the amino group of the amino acid is converted to an imine via reaction with the aldehyde R$^2$CHO and then any unreacted amino groups are capped with acetic anhydride to provide for compound 52. Compound 52 undergoes pyrollidine formation as described by Gallop, et al.[13]. The amino group of the pyrollidine compound is then protected via reaction with Fmoc-Cl and afterwards, the Alloc group removed as described above. Incorporation of a third tag ($^3$R$_2$NH, T$_3$) is accomplished via the methods described above to yield coded resin bound pyrrolidine compound 53. Conventional cleavage of this compound from the solid support via TFA yields soluble pyrrolidine compound 54.

Figure 10:
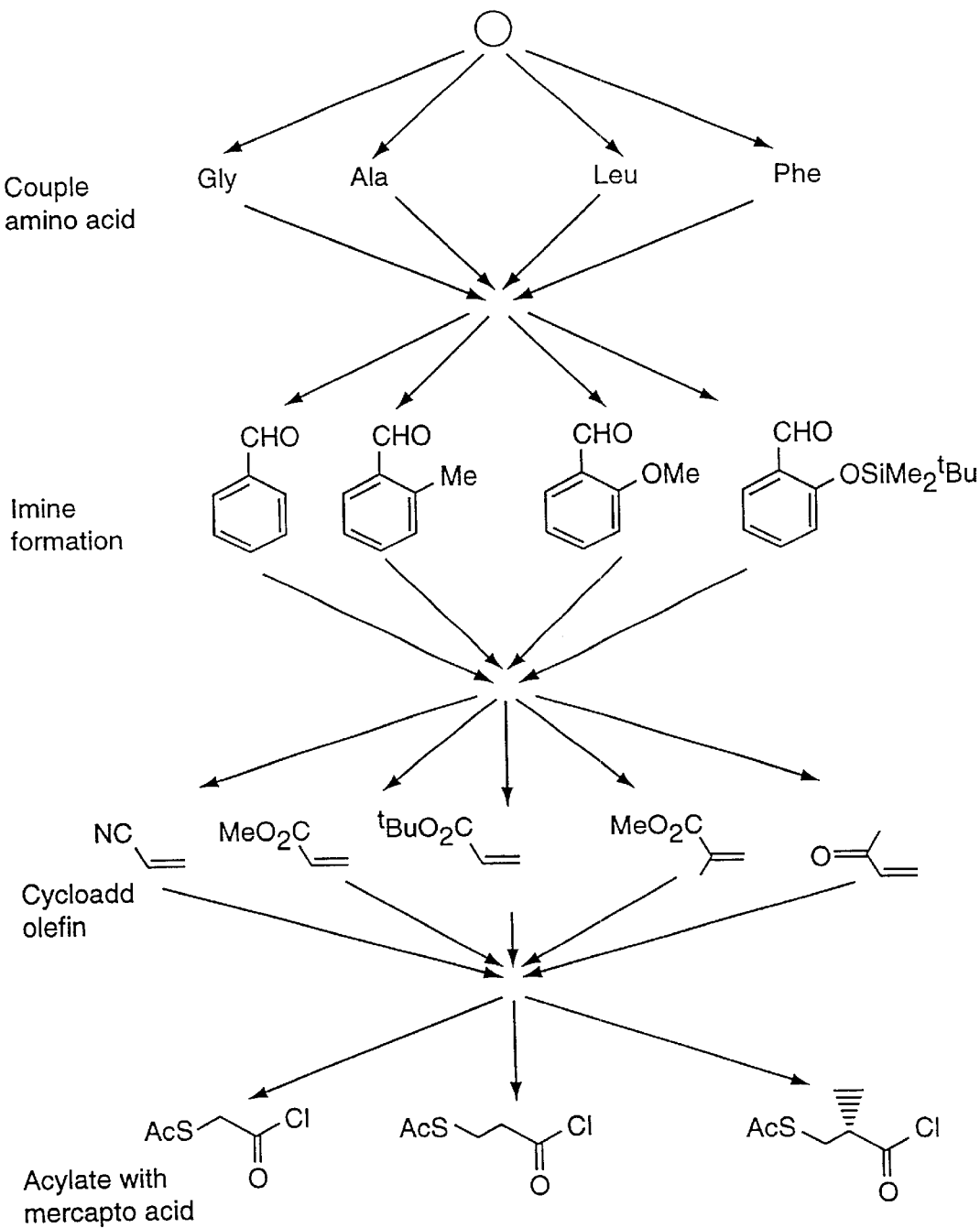

FIG. 10 illustrates the combinatorial approach for preparing the pyrrolidine library using the methods described above wherein each of the different components employed are exemplified.

FIG. 11 illustrates the coding scheme used for each of the different components during the synthesis as described above.

What is claimed is:

1. A method for tagging a solid support having multiple copies of a single target compound covalently attached thereto in order to determine the structure of the target compound attached to the support wherein the compound is prepared in situ on the support by sequentially conducting n reactions on said support wherein n is an integer greater than 1 which method comprises:

a) conducting a first reaction on the solid support wherein the first reaction and/or the step in the chemical synthesis where said reaction is conducted is encoded by a tag coupled to the support, immediately before or after coupling of each monomer, wherein said tag is an amine or mixture of amines selected from a plurality of amines of formula I

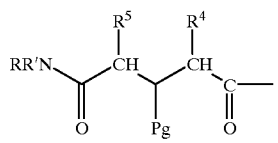

wherein R and R' are independently hydrocarbyl groups of from 1 to 30 carbon atoms which define a unique amine tag used to identify the reaction conducted in target compound synthesis and/or the point in time where said reaction is conducted; R4 and R5 are either hydrogen or are joined together with atoms in between to form a piperidine ring; and Pg is selected from the group consisting of hydrogen, an amine tag of formula I above bound to the amino nitrogen through the carbonyl functionality of formula I, and a compatible protecting group provided that the compatible protecting group is orthogonal to any and all protecting groups employed in compound synthesis, provided that each tag combination employed to encode a single reaction is different from and distinguishable over all other tag combinations used to encode other variations used in that reaction and still further provided that the amine compounds used to encode a first reaction are different from the amine compounds used to encode the other encrypted reactions so as provide a binary or higher coding system; and b) repeating procedure a) above until all n steps for target compound synthesis on the support are completed.

2. The method according to claim 1 wherein said amine or mixtures of amines of formula I are attached to the solid support via amide bonds.

3. The method according to claim 2 wherein said amide bonds are released from the resin by hydrolysis of the amide bond to produce amines of the formula HNRR'.

4. The method according to claim 3 wherein said amines are converted to a fluorescent entity.

5. The method according to claim 4 wherein said fluorescent entity is a dansylated derivative of the amine.

6. The method according to claim 5 wherein said dansylated derivatives are detected via HPLC using a fluorescent detector.

7. The method according to claim 4 wherein said amines are converted to perfluorobenzylamides.

8. The method according to claim 7 wherein said amides are detected via GC/MS.

9. The method according to claim 3 wherein said amines are detected via mass spectroscopy (MS).

10. The method according to claim 7 wherein said amides are detected via GC/MS.

11. A method for tagging a solid support having multiple copies of a single target compound covalently attached thereto in order to determine the structure of the target compound attached to the support wherein the compound is prepared in situ on the support by sequentially conducting n reactions on said support wherein n is an integer greater than 1 which method comprises:

a) conducting a first reaction on the solid support wherein the first reaction and/or the step in the chemical synthesis where said reaction is conducted is encoded by a tag coupled to the support, immediately before or after coupling of each monomer, wherein said tag is an amine or mixture of amines selected from a plurality of amines of formula I or formula II

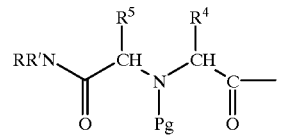

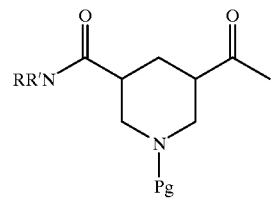

wherein R and R' are independently hydrocarbyl groups of from 1 to 30 carbon atoms which define a unique amine tag used to identify the reaction conducted in target compound synthesis and/or the point in time where said reaction is conducted; R4 and R5 are either hydrogen or are joined together with atoms in between to form a piperidine ring; and Pg is selected from the group consisting of hydrogen, an amine tag of formula I or II above bound to the amino nitrogen through the carbonyl functionality of formula I or II, and a compatible protecting group, provided that each tag combination employed to encode a single reaction is different from and distinguishable over all other tag combinations used to encode other variations used in that reaction and still further provided that the amine compounds used to encode a first reaction are different from the amine compounds used to encode the other encrypted reactions so as provide a binary or higher coding system; and b) repeating procedure a) above until all n steps for target compound synthesis on the support are completed.

12. The method according to claim 11 wherein said amine or mixtures of amines of formula I or II are attached to the solid support via amide bonds.

13. The method according to claim 12 wherein said amide bonds are released from the resin by hydrolysis of the amide bond to produce amines of the formula HNRR'.

14. The method according to claim 13 wherein said amines are converted to a fluorescent entity.

15. The method according to claim 14 wherein said fluorescent entity is a dansylated derivative of the amine.

16. The method according to claim 15 wherein said dansylated derivatives are detected via HPLC using a fluorescent detector.

17. The method according to claim 14 wherein said amines are converted to perfluorobenzylamides.

18. The method according to claim 17 wherein said amines are converted to perfluorobenzylamides.

19. The method according to claim 11 wherein said amines are detected via mass spectroscopy (MS).

* * * * *